(12) United States Patent
Clarke

(10) Patent No.: US 10,941,177 B2
(45) Date of Patent: *Mar. 9, 2021

(54) 2'-SUBSTITUTED CARBA-NUCLEOSIDE ANALOGS FOR ANTIVIRAL TREATMENT

(71) Applicant: Gilead Sciences, Inc., Foster City, CA (US)

(72) Inventor: Michael O' Neil Hanrahan Clarke, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/016,369

(22) Filed: Jun. 22, 2018

(65) Prior Publication Data

US 2019/0016749 A1    Jan. 17, 2019

Related U.S. Application Data

(63) Continuation of application No. 15/282,492, filed on Sep. 30, 2016, now abandoned, which is a continuation of application No. 13/793,557, filed on Mar. 11, 2013, now Pat. No. 9,481,704.

(60) Provisional application No. 61/610,411, filed on Mar. 13, 2012.

(51) Int. Cl.
  *C07H 19/23* (2006.01)
  *A61K 31/706* (2006.01)
  *A61K 45/06* (2006.01)
  *C07H 19/12* (2006.01)

(52) U.S. Cl.
  CPC ........... *C07H 19/23* (2013.01); *A61K 31/706* (2013.01); *A61K 45/06* (2013.01); *C07H 19/12* (2013.01)

(58) Field of Classification Search
  None
  See application file for complete search history.

(56) References Cited

U.S. PATENT DOCUMENTS

| | | |
|---|---|---|
| 8,008,264 B2 | 8/2011 | Butler et al. |
| 8,012,941 B2 | 9/2011 | Cho et al. |
| 8,318,682 B2 | 11/2012 | Butler et al. |
| 9,481,704 B2 | 11/2016 | Clarke |
| 2003/0087873 A1 | 5/2003 | Stuyver et al. |
| 2005/0196382 A1 | 9/2005 | Vaillant et al. |
| 2009/0317361 A1 | 12/2009 | Cho et al. |
| 2010/0021425 A1 | 1/2010 | Butler et al. |
| 2011/0230654 A1 | 9/2011 | Butler et al. |
| 2011/0269707 A1 | 11/2011 | Stuyver et al. |
| 2011/0293563 A1 | 12/2011 | Butler et al. |
| 2012/0009147 A1* | 1/2012 | Cho ................... A61K 31/7056 424/85.4 |
| 2012/0107274 A1 | 5/2012 | Clarke et al. |
| 2013/0034521 A1 | 2/2013 | Butler et al. |
| 2017/0114086 A1 | 4/2017 | Clarke |

FOREIGN PATENT DOCUMENTS

| | | | |
|---|---|---|---|
| CN | 101084232 A | 12/2007 | |
| CN | 102046626 A | 5/2011 | |
| WO | WO-2002/32920 A2 | 4/2002 | |
| WO | WO-2003/062257 A1 | 7/2003 | |
| WO | WO-2009/132123 A1 | 10/2009 | |
| WO | WO-2009/132135 A1 | 10/2009 | |
| WO | WO-2010/036407 A2 | 4/2010 | |
| WO | WO-2011035231 A1 * | 3/2011 | ............. A61P 31/14 |
| WO | WO-2012/037038 A1 | 3/2012 | |

OTHER PUBLICATIONS

International Search Report of PCT/US2013/030196 dated Jun. 26, 2913 (5 pages).
Office Action dated Aug. 14, 2015 for Chinese App. No. 201380014318.9.
Shi, J., et al., (2005), "Synthesis and anti-viral activity of a series of d-and 1-2'-deoxy-2'-fluororibonucleosides in the subgenomic HCV replicon system", *Bioorganic & medicinal chemistry*, 13:1641-52.
Written Opinion of PCT/US2013/030196 dated Jun. 26, 2013 (6 pages).
Extended European Search Report of European Application No. 16203290.8 dated Jun. 8, 2017 (9 pages).
Office Action of Mexican Application No. MX/a/2014/011009 dated Aug. 21, 2017.
Office Action of Chinese Application No. 201611121597.0 dated Mar. 15, 2018.

(Continued)

*Primary Examiner* — Dale R Miller

(57) ABSTRACT

Provided are compounds of Formula I,

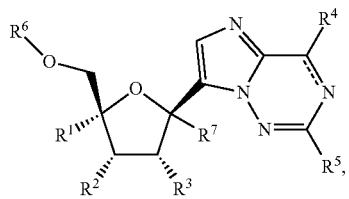

as well as pharmaceutical compositions containing compounds of Formula I and methods for treating Orthomyxoviridae virus infections by administering these compounds. The compounds, compositions, and methods provided are particularly useful for the treatment of Human Influenza virus infections.

25 Claims, No Drawings

(56) References Cited

OTHER PUBLICATIONS

Office Action dated Oct. 3, 2018 for Japanese Appl. No. 2017-121389.
Examination Report dated Jan. 10, 2019 for Canadian Appl. No. 2,866,381.
First Examination Report dated Dec. 10, 2018 for Indian Appl. No. 8505/DELNP/2014.
Examination Report of Australian Application No. 2017279590 dated Sep. 5, 2018.
Office Action of Chinese Application No. 201611121597.0 dated Sep. 25, 2018.
Office Action dated Apr. 16, 2019 for Korean Appl. No. 10-2014-7028523.
Office Action dated Mar. 20, 2019 for Chinese Appl. No. 201611121597.0.
Office Action dated Dec. 4, 2019 for Japanese Appl. No. 2018-242679.

* cited by examiner

2'-SUBSTITUTED CARBA-NUCLEOSIDE ANALOGS FOR ANTIVIRAL TREATMENT

This application is a Continuation of U.S. application Ser. No. 15/282,492 filed on Sep. 30, 2016, now abandoned, which is a Continuation of U.S. application Ser. No. 13/793,557 filed on Mar. 11, 2013, issued as U.S. Pat. No. 9,481,704, which claims the benefit of U.S. Provisional Application 61/610,411 filed on Mar. 13, 2012. The entire contents of each of these applications are incorporated herein by reference in their entireties.

FIELD OF THE INVENTION

The invention relates generally to compounds with antiviral activity, more particularly nucleosides active against Orthomyxoviridae virus infections, as well as pharmaceutical compositions and methods using the same.

BACKGROUND OF THE INVENTION

Influenza viruses of the Orthomyxoviridae family that belong to the genera A and B are responsible for seasonal flu epidemics each year, which cause acute contagious respiratory infections. Children, the old, and people with chronic diseases are at high risk to develop severe complications that lead to high morbidity and mortality rates (Memoli et al., *Drug Discovery Today* 2008, 13, 590-595). Among the three influenza genera, type A viruses are the most virulent human pathogens that cause the most severe disease, can be transmitted to other species, and give rise to human influenza pandemics. The recent human influenza outbreak of the aggressive porcine A/H1N1 strain in 2009 has emphasized the need for novel antiviral therapeutics. While yearly vaccination programs are currently used to protect populations from influenza infection, these programs must anticipate the virus strains that will be prevalent during seasonal outbreaks to be effective and they do not address the problem of sudden, unanticipated influenza pandemics. Again, the recent human influenza outbreak of the aggressive porcine A/H1N1 strain in 2009 is an example of this problem.

Several anti-influenza therapeutics are now available and others are under development (Hedlund et al., *Viruses* 2010, 2, 1766-1781). Among the currently available anti-influenza therapeutics are the M2 ion channel blockers amantadine and rimantadine and the neuraminidase inhibitors oseltamivir and zanamivir. However, resistance has developed to all of these medications. Therefore, there is a continuing need for novel anti-influenza therapeutics.

Promising new anti-influenza agents with novel mechanisms of action are now in development. Among these new agents is favipiravir, which targets viral gene replication by inhibiting influenza RNA polymerase. However, it is still uncertain whether this investigational drug candidate will become available for therapy. Therefore, there is a continuing need to develop additional compounds that inhibit influenza through this mechanism of action.

Certain ribosides of the nucleobases pyrrolo[1,2-f][1,2,4]triazine, imidazo[1,5-f][1,2,4]triazine, imidazo[1,2-f][1,2,4]triazine, and [1,2,4]triazolo[4,3-f][1,2,4]triazine have been disclosed in *Carbohydrate Research* 2001, 331(1), 77-82; *Nucleosides & Nucleotides* 1996, 15(1-3), 793-807; *Tetrahedron Letters* 1994, 35(30), 5339-42; *Heterocycles* 1992, 34(3), 569-74; *J. Chem. Soc. Perkin Trans.* 1 1985, 3, 621-30; *J. Chem. Soc. Perkin Trans.* 1 1984, 2, 229-38; WO 2000056734; *Organic Letters* 2001, 3(6), 839-842; *J Chem.* *Soc. Perkin Trans.* 1 1999, 20, 2929-2936; and *J. Med. Chem.* 1986, 29(11), 2231-5. However, these compounds have not been disclosed as useful for the treatment of Orthomyxoviridae infections.

Ribosides of pyrrolo[1,2-f][1,2,4]triazinyl, imidazo[1,5-f][1,2,4]triazinyl, imidazo[1,2-f][1,2,4]triazinyl, and [1,2,4]triazolo[4,3-f][1,2,4]triazinyl nucleobases with antiviral, anti-HCV, and anti-RdRp activity have been disclosed by Babu, WO2008/089105 and WO2008/141079, Cho et al., WO2009/132123, and Francom et al. WO2010/002877. Butler et al., WO2009/132135, discloses anti-viral pyrrolo[1,2-f][1,2,4]triazinyl, imidazo[1,5-f][1,2,4]triazinyl, imidazo[1,2-f][1,2,4]triazinyl, and [1,2,4]triazolo[4,3-f][1,2,4]triazinyl nucleosides wherein the 1' position of the nucleoside sugar is substituted with a cyano or methyl group. However, the effectiveness of these compounds for the treatment of Orthomyxoviridae infections has not been disclosed.

SUMMARY OF THE INVENTION

Provided herein are compounds that inhibit viruses of the Orthomyxoviridae family. The invention also comprises compounds of Formula I that inhibit viral nucleic acid polymerases, particularly Orthomyxoviridae RNA-dependent RNA polymerase (RdRp), rather than cellular nucleic acid polymerases. Compounds of Formula I are useful for treating Orthomyxoviridae infections in humans and other animals.

The first embodiment of the invention is directed to a compound of Formula I:

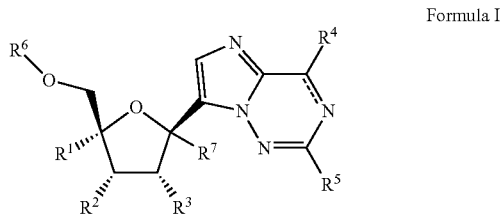

Formula I or a pharmaceutically acceptable salt, solvate, or ester thereof;
wherein:
each of $R^1$ and $R^7$ is independently H, halogen, $OR^a$, $(C_1-C_8)$haloalkyl, CN, $N_3$, $(C_1-C_8)$alkyl, $(C_1-C_8)$substituted alkyl, $(C_2-C_8)$alkenyl, $(C_2-C_8)$substituted alkenyl, $(C_2-C_8)$alkynyl or $(C_2-C_8)$substituted alkynyl, wherein the substituent is selected from the group consisting of —X, —$R^b$, —OH, =O, —$OR^b$, —$SR^b$, —$S^-$, —$NR^b_2$, —$N^+R^b_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b_2$, —S(=O)$_2$—, —S(=O)$_2$OH, —S(=O)$_2R^b$, —OS(=O)$_2OR^b$, —S(=O)$_2NR^b_2$, —S(=O)$R^b$, —OP(=O)(OR^b)$_2$, —P(=O)(OR^b)$_2$, —P(=O)(O$^-$)$_2$, —P(=O)(OH)$_2$, —P(O)(OR^b)(O$^-$), —C(=O)$R^b$, —C(=O)X, —C(S)$R^b$, —C(O)$OR^b$, —C(O)O—, —C(S)$OR^b$, —C(O)$SR^b$, —C(S)$SR^b$, —C(O)$NR^b_2$, —C(S)$NR^b_2$, —C(=$NR^b$)$NR^b_2$, where each X is independently a halogen: F, Cl, Br, or I; and each $R^b$ is independently H, alkyl, aryl, arylalkyl, a heterocycle, or a protecting group or prodrug moiety;

$R^2$ is $OR^a$;

$R^3$ is halogen or $N_3$;

each $R^a$ is independently H, aryl, arylalkyl, or $(C_1-C_8)$ alkyl;

each of $R^4$ and $R^5$ is independently H, =O, $OR^a$, $N(R^a)_2$, $N_3$, CN, $S(O)_nR^a$, halogen, or $(C_1-C_8)$haloalkyl;

n is 0, 1 or 2; and $R^6$ is H, aryl, arylalkyl, or

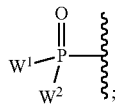

wherein $W^1$ and $W^2$ are each, independently, $OR^a$ or a group of the Formula Ia:

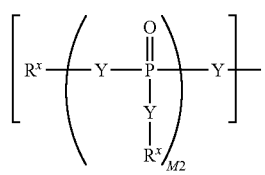

Formula Ia wherein:

each Y is independently a bond or O;

M2 is 0, 1 or 2;

each $R^x$ is H, halogen or OH.

In a preferred embodiment, the compound of Formula I is represented by Formula II:

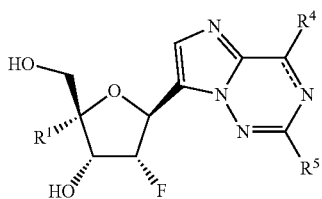

Formula II or a pharmaceutically acceptable salt, solvate, or ester thereof. In other preferred embodiments, $R^1$ is H, $R^2$ is OH or O-benzyl and/or $R^3$ is F or $N_3$ and, more preferably, $R^3$ is F. In a certain embodiment of the present invention, $R^4$ is $NH_2$ and $R^5$ is H, F, Cl, Br, $N_3$, CN, $CF_3$, $NH_2$, SMe, or $SO_2Me$, and, in another embodiment, $R^5$ is $NH_2$ and $R^4$ is =O, OH, OMe, Cl, Br, I, $NH_2$, NHMe, NHcPr or SMe. In still further preferred embodiments, $R^4$ and $R^5$ are both $NH_2$ or SMe, $R^5$ is H, or $R^4$ is =O. In other preferred embodiments, $R^6$ is H, benzyl, or

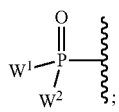

wherein $W^2$ is OH and W is a group of the Formula Ia:

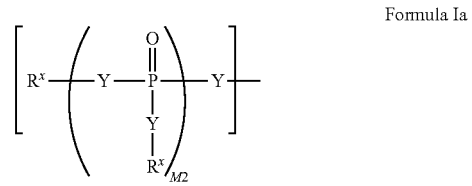

Formula Ia wherein each Y is O; M2 is 2; and each $R^x$ is H. In another embodiment, $R^7$ is H or OH.

The second embodiment of the invention is directed to a pharmaceutical composition comprising a therapeutically effective amount of a compound of Formula I, II or III, as defined in the first embodiment of the invention, and a pharmaceutically acceptable carrier or excipient. In a certain embodiment thereof, the pharmaceutical composition further comprises at least one additional therapeutic agent.

The third embodiment of the invention is directed to a method for treating an Orthomyxoviridae infection in a mammal in need thereof comprising administering a therapeutically effective amount of a compound of Formula I, II or III or a pharmaceutically acceptable salt, solvate or ester thereof, as defined in the first embodiment of the invention. In some embodiments, the Orthomyxoviridae infection being treated is an Influenza virus A infection, an Influenza virus B infection, or an Influenza virus C infection. In another embodiment, the method comprises treating an Orthomyxoviridae infection in a mammal in need thereof by administering a therapeutically effective amount of a pharmaceutical composition comprising an effective amount of a Formula I, II or III compound or a pharmaceutically acceptable salt, solvate or ester thereof in combination with a pharmaceutically acceptable diluent or carrier.

In another embodiment, the present invention provides a method of inhibiting an Orthomyxoviridae RNA-dependent RNA polymerase. In a further embodiment, this method comprises contacting a cell infected with Orthomyxoviridae virus with an effective amount of a compound of Formula I, II or III or a pharmaceutically acceptable salt, solvate, or ester thereof.

In another aspect of this embodiment, the present invention provides a method of treating an Orthomyxoviridae virus infection and, in a certain embodiment, further comprises administering a therapeutically effective amount of at least one additional therapeutic agent or composition thereof selected from the group consisting of a corticosteroid, an anti-inflammatory signal transduction modulator, a β2-adrenoreceptor agonist bronchodilator, an anticholinergic, a mucolytic agent, hypertonic saline, an agent that inhibits migration of pro-inflammatory cells to the site of infection, and mixtures thereof. In certain embodiments, the additional therapeutic agent is a viral haemagglutinin inhibitor, a viral neuramidase inhibitor, a M2 ion channel inhibitor, a Orthomyxoviridae RNA-dependent RNA polymerase inhibitor or a sialidase. In another embodiment, the additional therapeutic agent is selected from the group consisting of ribavirin, oseltamivir, zanamivir, laninamivir, peramivir, amantadine, rimantadine, CS-8958, favipiravir, AVI-7100, alpha-1 protease inhibitor and DAS181.

In another embodiment of the invention, the compound of Formula I, II or III and/or at least one additional therapeutic agent is administered by inhalation.

DETAILED DESCRIPTION OF THE INVENTION

The first embodiment of the present invention is directed to a compound of Formula I:

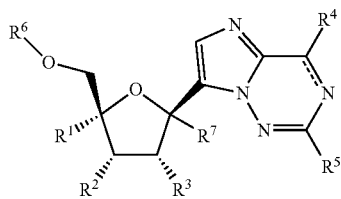

Formula I or a pharmaceutically acceptable salt, solvate, or ester thereof; wherein:

each of $R^1$ and $R^7$ is independently H, halogen, $OR^a$, $(C_1-C_8)$haloalkyl, CN, $N_3$, $(C_1-C_8)$alkyl, $(C_1-C_8)$substituted alkyl, $(C_2-C_8)$alkenyl, $(C_2-C_8)$substituted alkenyl, $(C_2-C_8)$alkynyl or $(C_2-C_8)$substituted alkynyl, wherein the substituent is selected from the group consisting of —X, —$R^b$, —OH, =O, —$OR^b$, —$SR^b$, —$S^-$, —$NR^b_2$, —$N^+R^b_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b_2$, —S(=O)$_2$—, —S(=O)$_2$OH, —S(=O)$_2R^b$, —OS(=O)$_2OR^b$, —S(=O)$_2NR^b_2$, —S(=O)$R^b$, —OP(=O)($OR^b$)$_2$, —P(=O)($OR^b$)$_2$, —P(=O)($O^-$)$_2$, —P(=O)(OH)$_2$, —P(O)($OR^b$)($O^-$), —C(=O)$R^b$, —C(=O)X, —C(S)$R^b$, —C(O)$OR^b$, —C(O)O—, —C(S)$OR^b$, —C(O)$SR^b$, —C(S)$SR^b$, —C(O)$NR^b_2$, —C(S)$NR^b_2$, —C(=$NR^b$)$NR^b_2$, where each X is independently a halogen: F, Cl, Br, or I; and each $R^b$ is independently H, alkyl, aryl, arylalkyl, a heterocycle, or a protecting group or prodrug moiety;

$R^2$ is $OR^a$;

$R^3$ is halogen or $N_3$;

each $R^a$ is independently H, aryl, arylalkyl, or $(C_1-C_8)$alkyl;

each of $R^4$ and $R^5$ is independently H, =O, $OR^a$, $N(R^a)_2$, $N_3$, CN, $S(O)_nR^a$, halogen, or $(C_1-C_8)$haloalkyl;

each n is 0, 1 or 2; and $R^6$ is H, aryl, arylalkyl, or

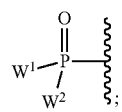

wherein $W^1$ and $W^2$ are each, independently, $OR^a$ or a group of the Formula Ia:

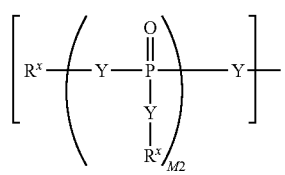

Formula Ia wherein:

each Y is independently a bond or O;

M2 is 0, 1 or 2; and each $R^x$ is H, halogen or OH. In regard to Formula Ia, when Y is O, $R^x$ is not halogen.

Unless stated otherwise, the following terms and phrases as used herein are intended to have the following meanings.

When trade names are used herein, applicants intend to independently include the tradename product and the active pharmaceutical ingredient(s) of the tradename product.

"Alkyl" is hydrocarbon containing normal, secondary, tertiary or cyclic carbon atoms. For example, an alkyl group can have 1 to 20 carbon atoms (i.e, $C_1-C_{20}$ alkyl), 1 to 8 carbon atoms (i.e., $C_1-C_8$ alkyl), or 1 to 6 carbon atoms (i.e., $C_1-C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), cyclopropyl (c-propyl, cPr), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, and octyl (—($CH_2$)$_7CH_3$).

"Alkenyl" is a hydrocarbon containing normal, secondary, tertiary or cyclic carbon atoms with at least one site of unsaturation, i.e., a carbon-carbon, $sp^2$ double bond. For example, an alkenyl group can have 2 to 20 carbon atoms (i.e., $C_2-C_{20}$ alkenyl), 2 to 8 carbon atoms (i.e., $C_2-C_8$ alkenyl), or 2 to 6 carbon atoms (i.e., $C_2-C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2-C_{20}$ alkynyl), 2 to 8 carbon atoms (i.e., $C_2-C_8$ alkyne), or 2 to 6 carbon atoms (i.e., $C_2-C_6$ alkynyl). Examples of suitable alkynyl groups include, but are not limited to, acetylenic (—C≡CH), propargyl (—$CH_2$C≡CH), and the like.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g., 1, 2, 3, or 4) carbon atoms have been replaced with a heteroatom (e.g., O, N, or S). The terms "heterocycle" or "heterocyclyl" includes saturated rings, partially unsaturated rings, and aromatic rings (i.e., heteroaromatic rings).

The term "substituted" in reference to alkyl, alkenyl, aryl, etc., for example, "substituted alkyl", "substituted alkenyl", "substituted aryl", respectively, in which one or more hydrogen atoms are each independently replaced with a non-hydrogen substituent. Typical substituents include, but are not limited to, —X, —$R^b$, —OH, =O, —$OR^b$, —$SR^b$, —$S^-$, —$NR^b{}_2$, —$N^+R^b{}_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b{}_2$, —S(=O)$_2$—, —S(=O)$_2$OH, —S(=O)$_2R^b$, —OS(=O)$_2OR^b$, —S(=O)$_2NR^b{}_2$, —S(=O)$R^b$, —OP(=O)(OR$^b$)$_2$, —P(=O)(OR$^b$)$_2$, —P(=O)(O$^-$)$_2$, —P(=O)(OH)$_2$, —P(O)(OR$^b$)(O$^-$), —C(=O)$R^b$, —C(=O)X, —C(S)$R^b$, —C(O)OR$^b$, —C(O)O$^-$, —C(S)OR$^b$, —C(O)SR$^b$, —C(S)SR$^b$, —C(O)NR$^b{}_2$, —C(S)NR$^b{}_2$, —C(=NR$^b$)NR$^b{}_2$, where each X is independently a halogen: F, Cl, Br, or I; and each $R^b$ is independently H, alkyl, aryl, arylalkyl, a heterocycle, or a protecting group or prodrug moiety.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{30}$ and acyloxymethyl carbonates —$CH_2OC(=O)OR^{30}$ where $R^{30}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was used as a prodrug strategy for carboxylic acids and then applied to phosphates and phosphonates by Farquhar et al., (1983) *J. Pharm. Sci.* 72: 324; also U.S. Pat. Nos. 4,816,570, 4,968, 788, 5,663,159 and 5,792,756. In certain compounds of the invention, a prodrug moiety is part of a phosphate group. The acyloxyalkyl ester may be used to deliver phosphoric acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —CH$_2$OC(=O)C(CH$_3$)$_3$. An exemplary acyloxymethyl carbonate prodrug moiety is pivaloyloxymethylcarbonate (POC) —CH$_2$OC(=O)OC(CH$_3$)$_3$.

The phosphate group may be a phosphate prodrug moiety. The prodrug moiety may be sensitive to hydrolysis, such as, but not limited to those comprising a pivaloyloxymethyl carbonate (POC) or POM group. Alternatively, the prodrug moiety may be sensitive to enzymatic potentiated cleavage, such as a lactate ester or a phosphonamidate-ester group.

One skilled in the art will recognize that substituents and other moieties of the compounds of Formula I should be selected in order to provide a compound which is sufficiently stable to provide a pharmaceutically useful compound which can be formulated into an acceptably stable pharmaceutical composition. Compounds of Formula I which have such stability are contemplated as falling within the scope of the present invention.

It is to be noted that all enantiomers, diastereomers, and racemic mixtures, tautomers, polymorphs, pseudopolymorphs of compounds within the scope of Formula I and pharmaceutically acceptable salts (as well as complexes, co-crystals, etc.), solvates or esters thereof are embraced by the present invention. All mixtures of such enantiomers and diastereomers are within the scope of the present invention.

A compound of Formula I and its pharmaceutically acceptable salts, solvates, or esters may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I and their pharmaceutically acceptable salts.

A compound of Formula I and its pharmaceutically acceptable salts, solvates or esters may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I and their pharmaceutically acceptable salts.

In a certain embodiment of the invention, the compound of Formula I is represented by Formula II:

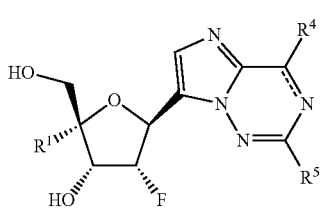

Formula II or a pharmaceutically acceptable salt, solvate, or ester thereof;

wherein the variables are as defined for Formula I. Preferably, R$^1$ in Formula II is H, R$^4$ is NH$_2$ or =O, and/or R$^5$ is NH$_2$ or H. More preferably, the compound is selected from the group consisting of

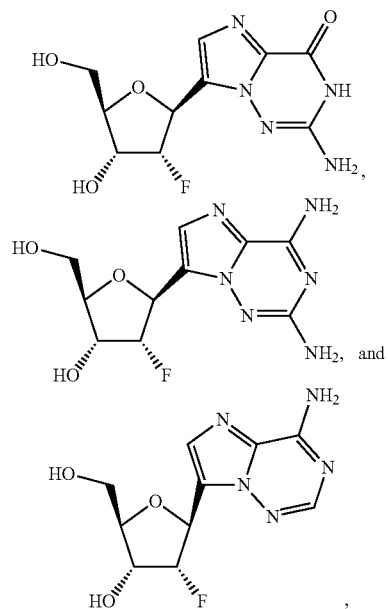

or a pharmaceutically acceptable salt, solvate, or ester thereof.

In a preferred embodiment of the compounds of Formula I, R$^1$ is H, CH$_2$OH, CH$_2$F, CHF$_2$, CH=CH$_2$, C≡CH, CN, CH$_2$CH=CH$_2$, N$_3$, CH$_3$ or CH$_2$CH$_3$, and, more preferably, R$^1$ is H.

In a further embodiment of the invention, R$^2$ is OH or O-benzyl, and, more preferably is OH.

In a further embodiment of the invention, R$^3$ is F or N$_3$, and, more preferably R$^3$ is F.

In a further preferred embodiment, R$^4$ and R$^5$ are selected from H, NH$_2$, =O, NHMe, NHcPr, OH, OMe, Cl, Br, I, SMe, F, N$_3$, CN, CF$_3$, and SO$_2$Me, and more preferably R$^4$ is =O or NH$_2$, and/or R$^5$ is H or NH$_2$.

In a further embodiment, R$^6$ is H, benzyl, or

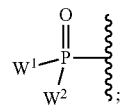

wherein W$^2$ is OH and W$^1$ is a group of the Formula Ia:

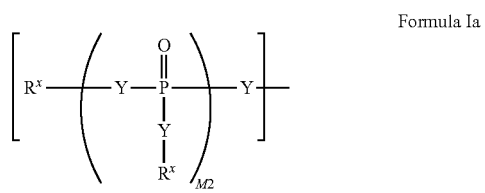

Formula Ia wherein:

Y is O;

M2 is 2; and each $R^x$ is H, and, more preferably, $R^6$ is H.

In a further embodiment of the invention, $R^7$ is H or OH, and, more preferably, $R^7$ is H.

In other preferred embodiments of the invention, $R^1$ is H, $R^2$ is OH and $R^3$ is F. In another preferred embodiment, $R^1$ is H, $R^2$ is OH, $R^3$ is F, $R^4$ and $R^5$ are $NH_2$, H or =O, and $R^6$ and $R^7$ are hydrogen.

In still another preferred embodiment, $R^1$ is H, $R^2$ is O-benzyl or OH, $R^3$ is F, $R^4$ is SMe, $NH_2$ or =O, $R^5$ is SMe, $SO_2Me$, H or $NH_2$, $R^6$ is benzyl or

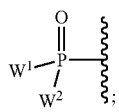

wherein $W^2$ is OH and $W^1$ is a group of the Formula Ia:

Formula Ia $$\left[ R^x \!-\!\!\left(\!Y\!-\!\!\overset{\overset{\displaystyle O}{\|}}{\underset{\underset{\displaystyle R^x}{|}}{\underset{\displaystyle |}{P}}}\!-\!Y\!\right)\!-\!Y\!\right]_{M2}$$

wherein:

Y is O;

M2 is 2; and each $R^x$ is H, and $R^7$ is H or OH.

In other certain embodiments of the invention, $R^4$ is $NH_2$ and $R^5$ is H, F, Cl, Br, $N_3$, CN, $CF_3$, $NH_2$, SMe, or $SO_2Me$, or $R^5$ is $NH_2$ and $R^4$ is =O, OH, OMe, Cl, Br, I, $NH_2$, NHMe, NHcPr or SMe. In preferred embodiments thereof, $R^4$ and $R^5$ are both $NH_2$ or SMe, $R^5$ is H, or $R^4$ is =O.

In another embodiment of the invention, $R^1$ is H, $R^2$ is O-benzyl, $R^3$ is F, $R^4$ is SMe, $NH_2$, OMe or $OCH_2CH_3$, $R^5$ is H, SMe, $SO_2Me$, $NH_2$, $N_3$ or F, $R^6$ is benzyl, and $R^7$ is H or OH.

In a preferred embodiment of the invention, the compound of Formula I is:

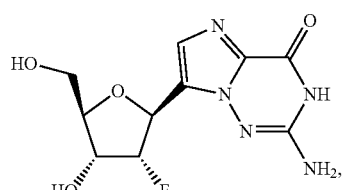

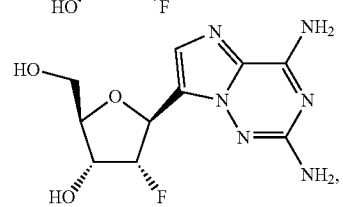

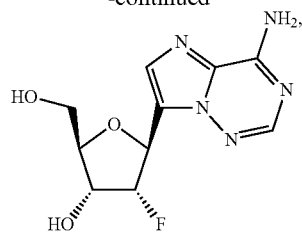

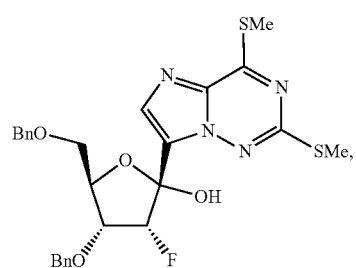

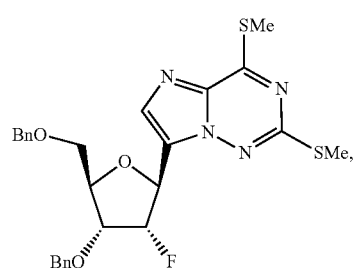

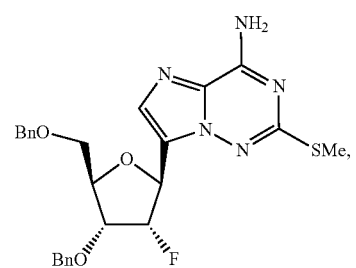

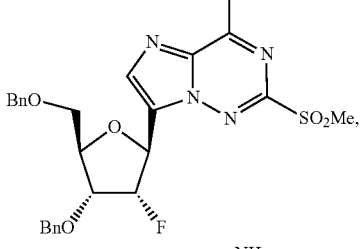

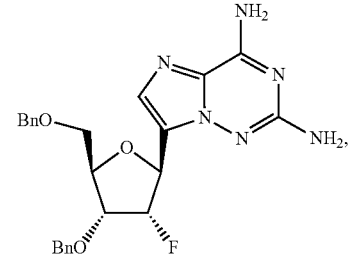

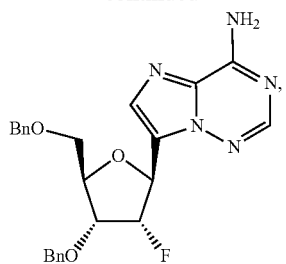
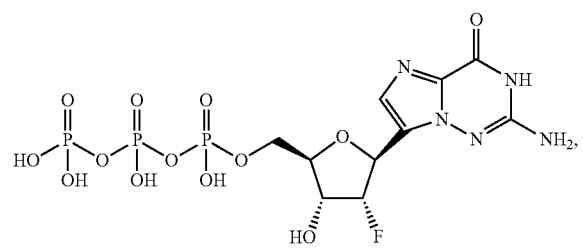
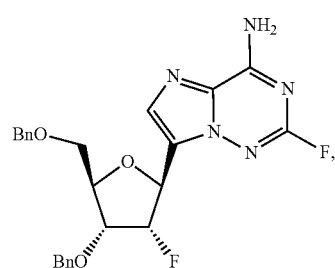
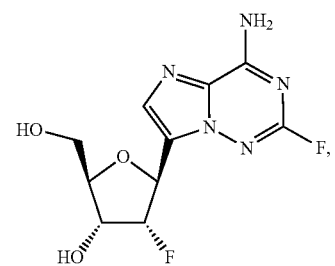
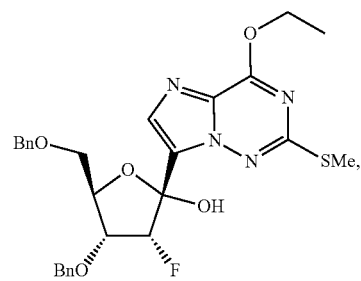
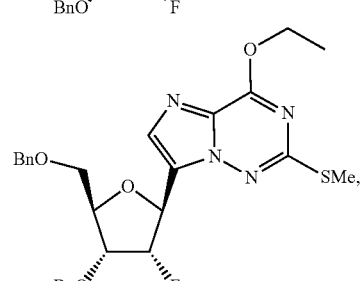
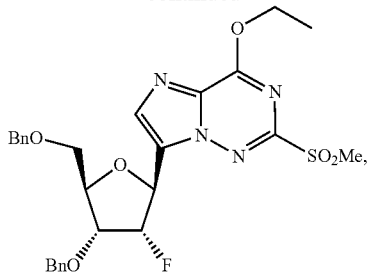
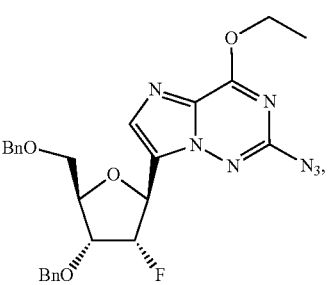
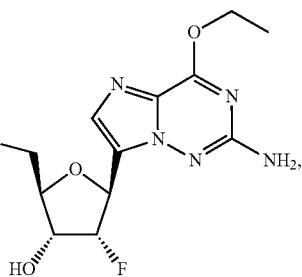
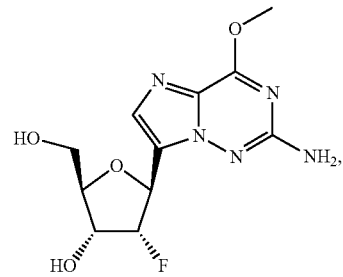
or a pharmaceutically acceptable salt, solvate, or ester thereof.
In another embodiment of the invention, the compound of Formula I is:
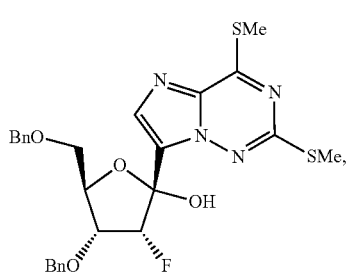

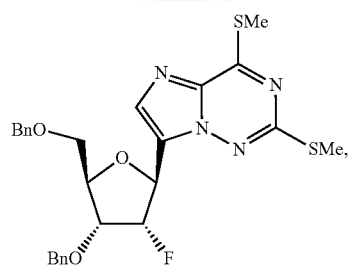
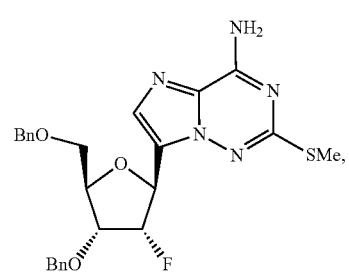
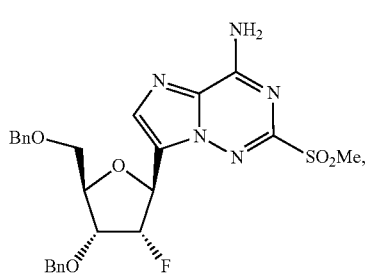
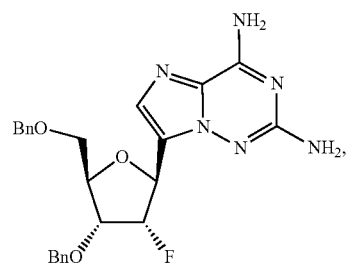
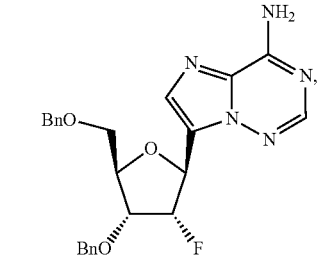
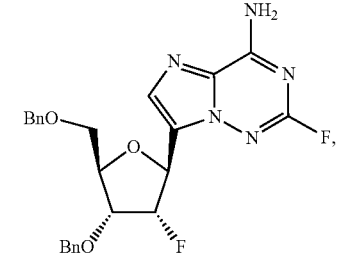
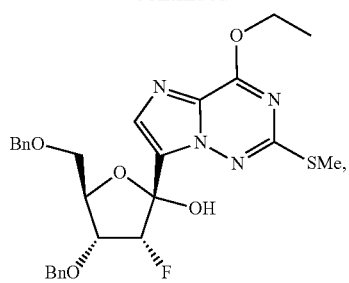
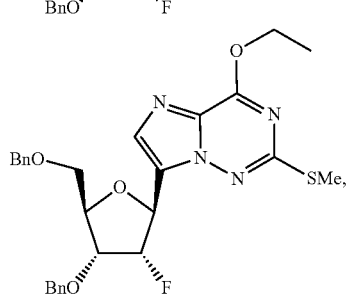
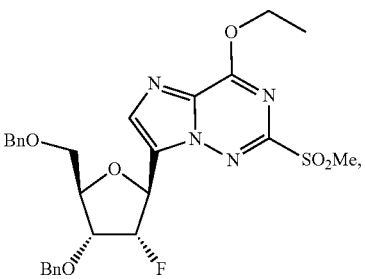
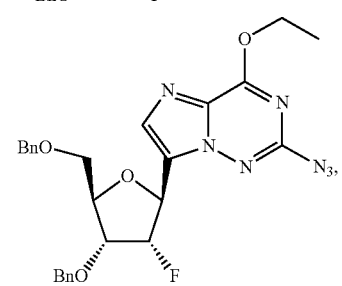
or a pharmaceutically acceptable salt, solvate, or ester thereof.
In a still further preferred embodiment of the invention, the compound of Formula I is:
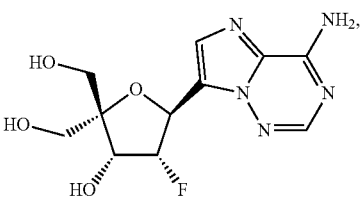
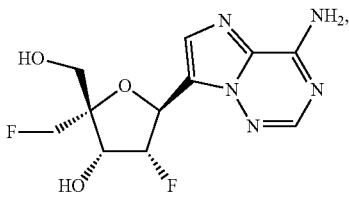

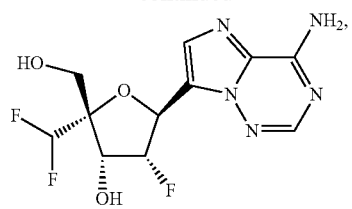
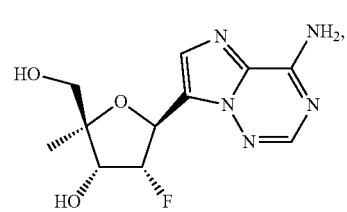
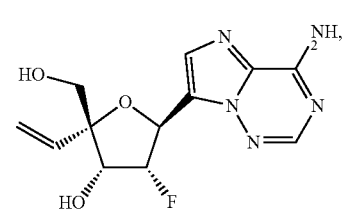
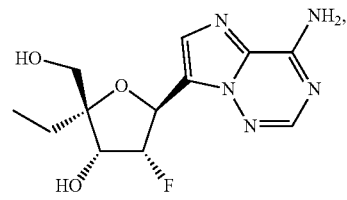
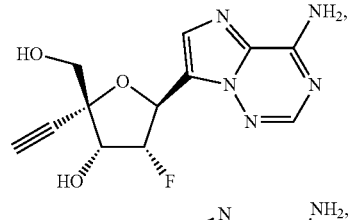
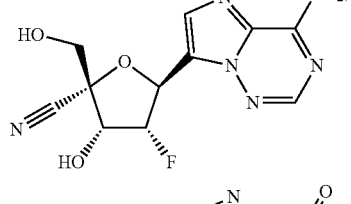
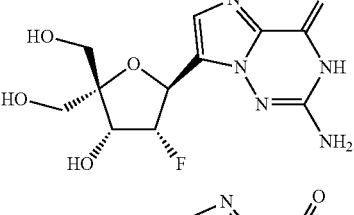
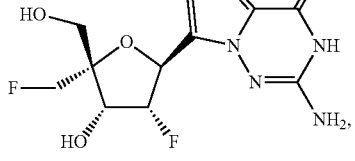
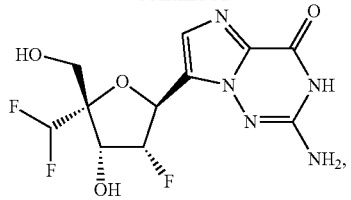
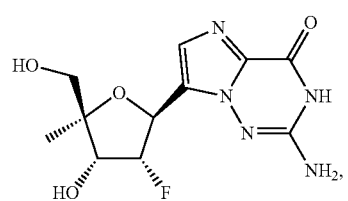
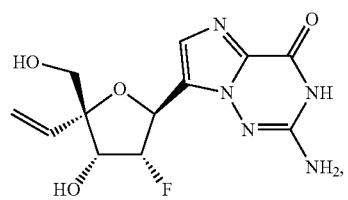
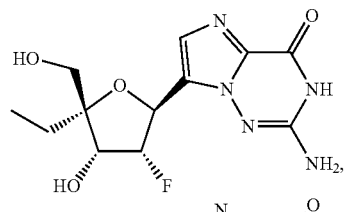
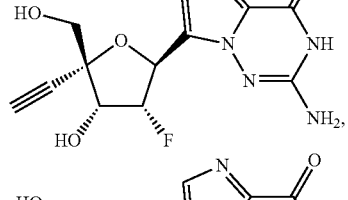
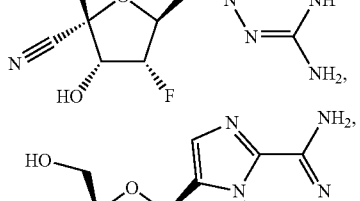
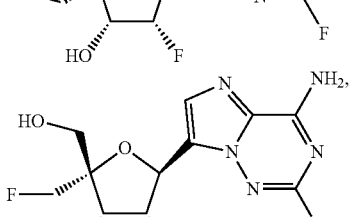

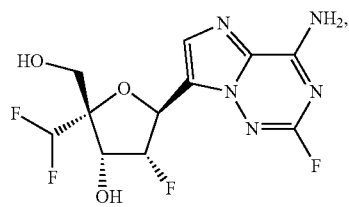
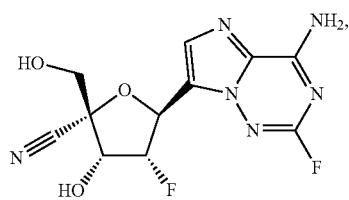
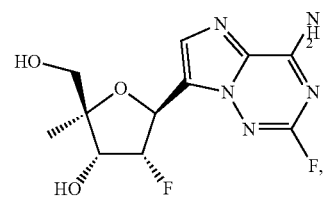
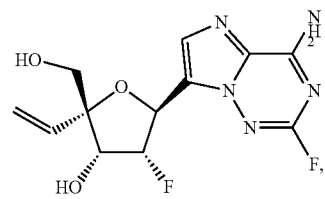
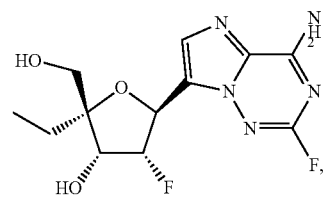
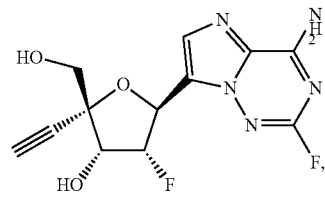
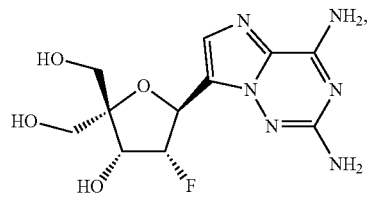
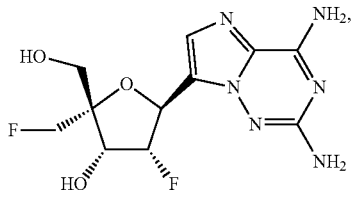
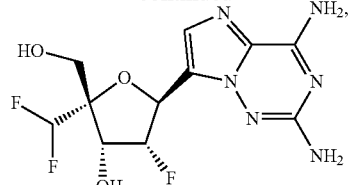
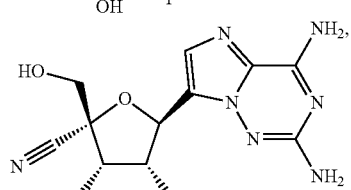
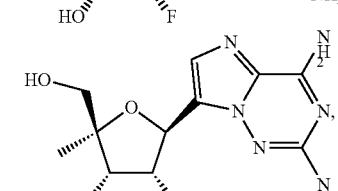
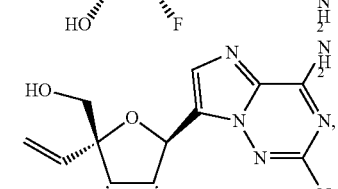
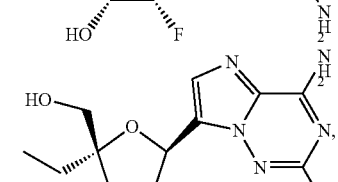
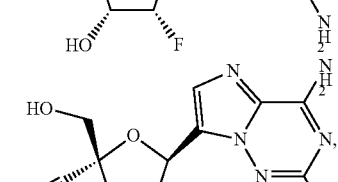
or a pharmaceutically acceptable salt, solvate, or ester thereof.
In a certain embodiment of the invention, the present invention is directed to compounds of Formula III:
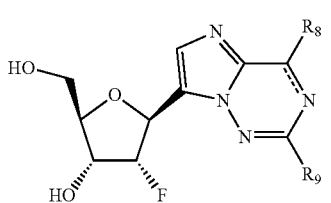
Formula III
wherein
$R^8$ is $NH_2$, OMe, $OCH_2CH_3$ or =O and
$R^9$ is $NH_2$, H, or F,
or a pharmaceutically acceptable salt, solvate, or ester thereof.

Preferably, the compound of Formula III is selected from the group consisting of

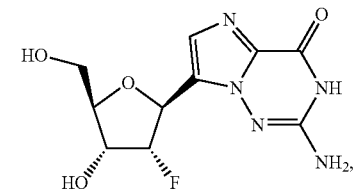

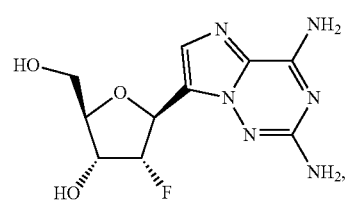

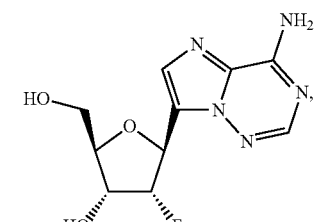

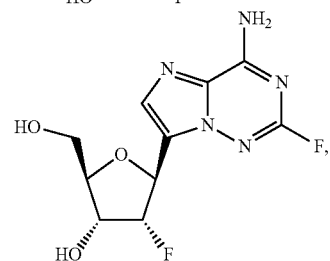

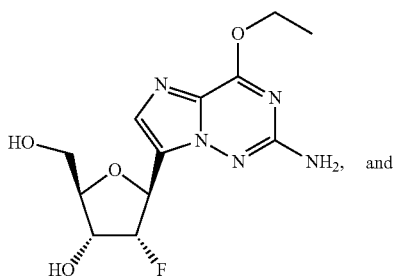

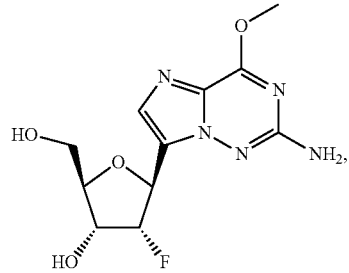

or a pharmaceutically acceptable salt, solvate, or ester thereof. More preferably, the compound of Formula III is selected from the group consisting of

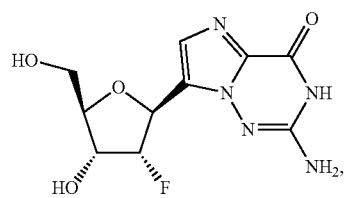

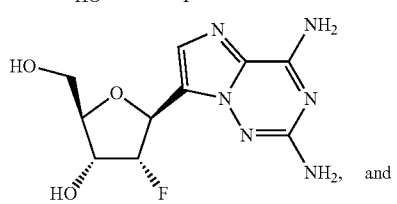

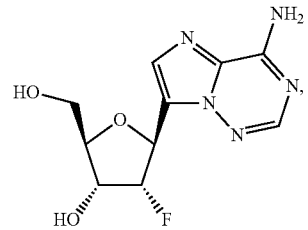

or a pharmaceutically acceptable salt, solvate, or ester thereof.

The second embodiment of the invention is directed to a pharmaceutical composition comprising a therapeutically effective amount of a compound of Formula I, as defined above with respect to the first embodiment of the invention, and a pharmaceutically acceptable carrier or excipient. In a certain embodiment thereof, the compound of Formula I is represented by Formula II or Formula III, as defined above with respect to the first embodiment of the invention. Terms in the second embodiment of the invention are defined as above with respect to the first embodiment of the invention. Preferred embodiments of $R^1$, $R^2$, $R^3$, $R^4$, $R^5$, $R^6$ and $R^7$ in the second embodiment of the invention are the same as for the first embodiment of the invention.

In a preferred embodiment of the second embodiment of the invention, the compound of Formula I is:

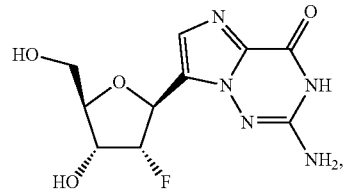

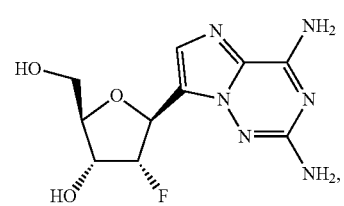

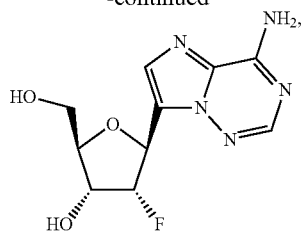
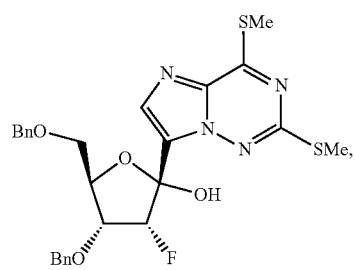
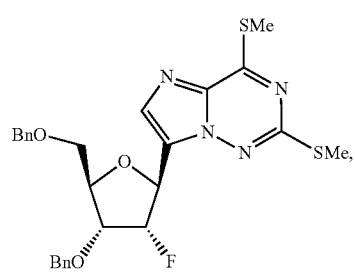
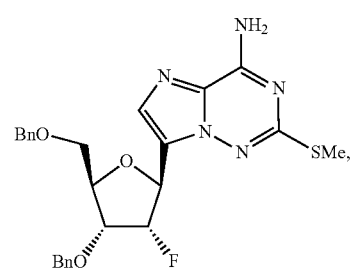
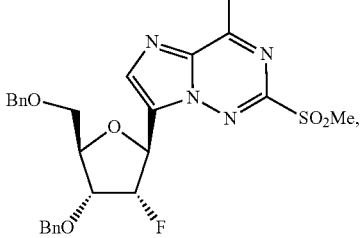
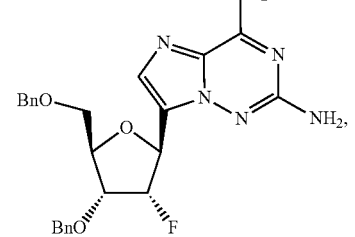
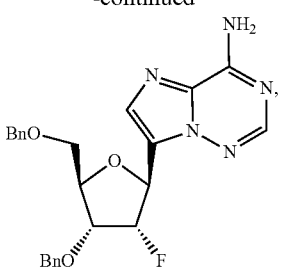
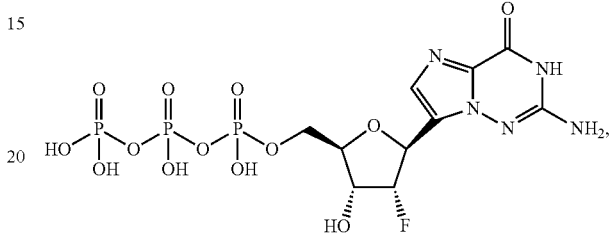
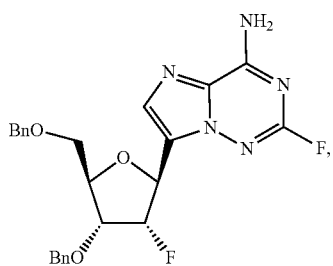
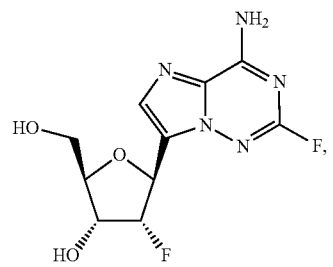
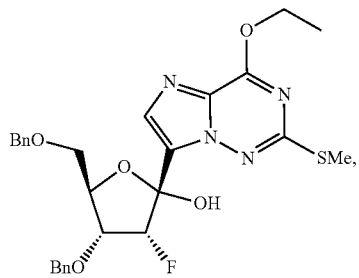
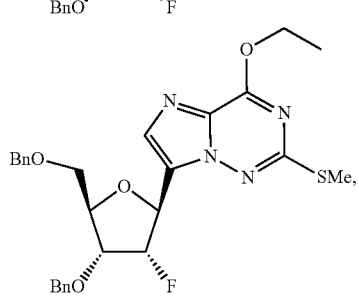

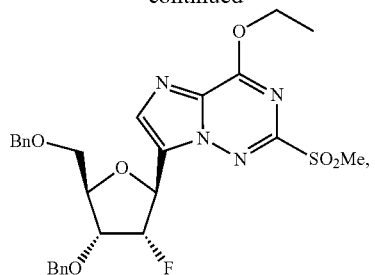
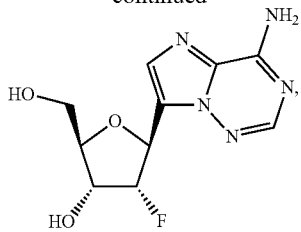
or a pharmaceutically acceptable salt, solvate, or ester thereof.
In another preferred embodiment of the invention, the compound of Formula I is:
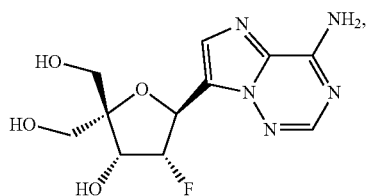
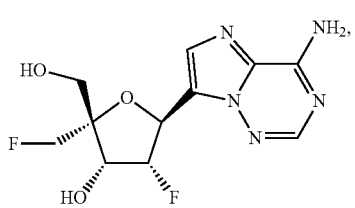
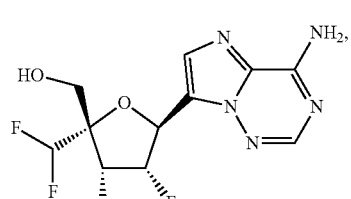
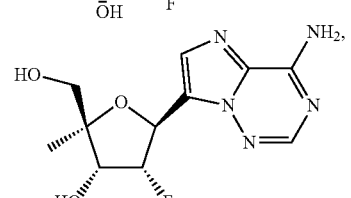
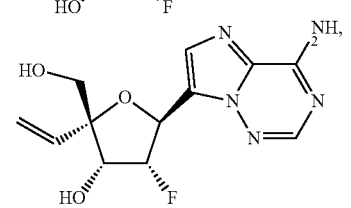
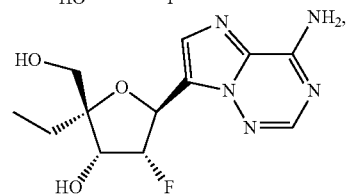
or a pharmaceutically acceptable salt, solvate, or ester thereof, and more preferably is

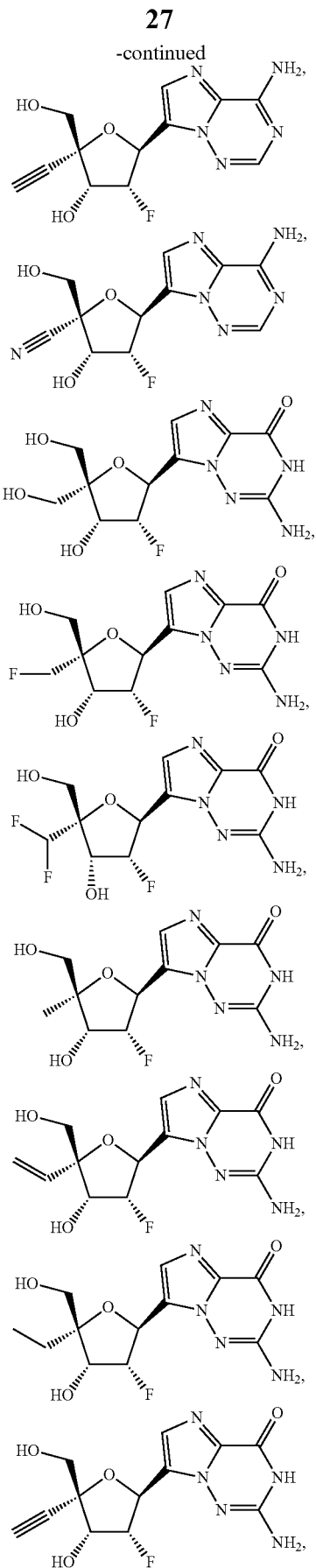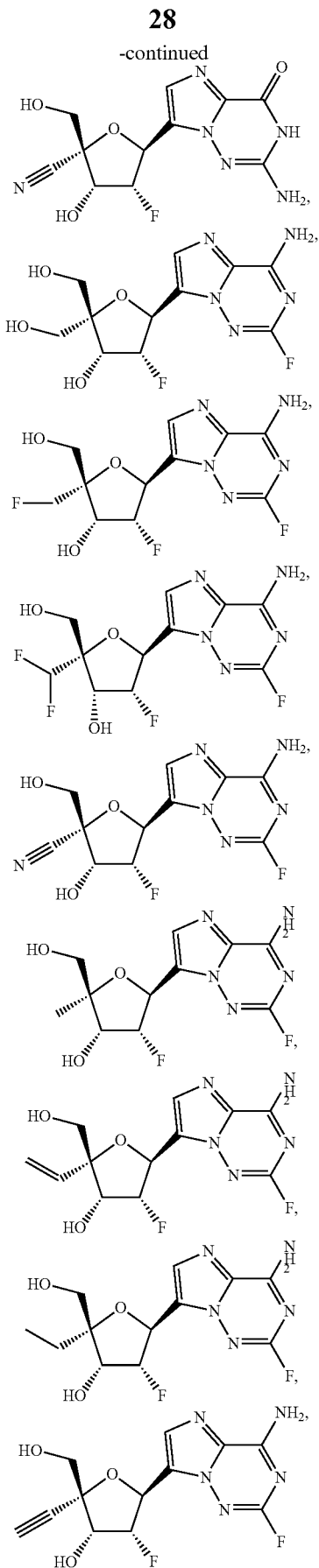

-continued

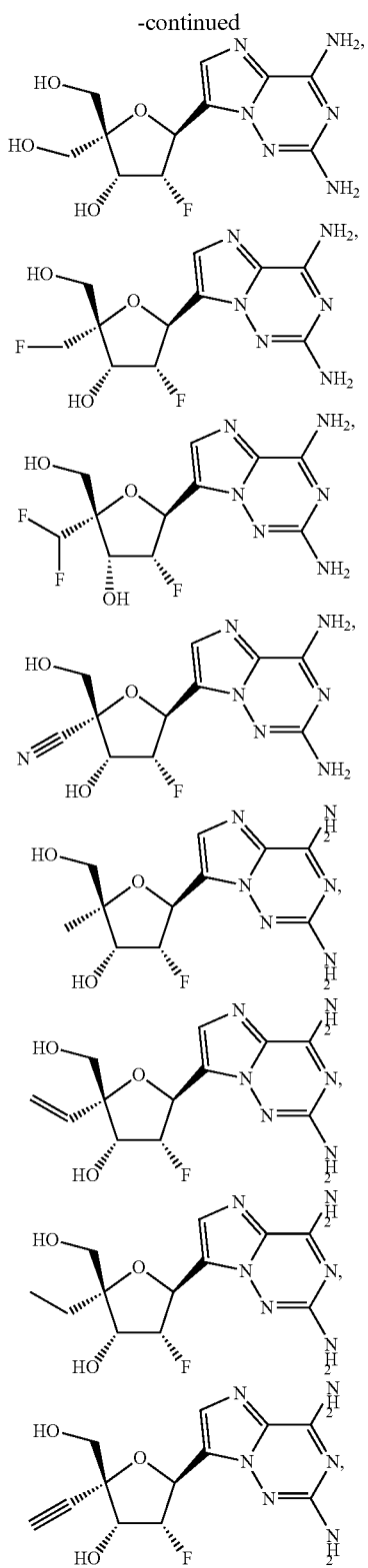

or a pharmaceutically acceptable salt, solvate, or ester thereof.

The terms "pharmaceutical composition" and "pharmaceutical formulation" are used interchangeably herein. Pharmaceutical compositions of the present invention contain compounds of this invention and may be formulated using any conventional carriers and excipients, which will be selected in accord with ordinary practice. Tablets will contain excipients, glidants, fillers, binders and the like. Aqueous pharmaceutical formulations are prepared in sterile form, and, when intended for delivery by other than oral administration, generally will be isotonic. All pharmaceutical formulations will optionally contain excipients such as those set forth in the "Handbook of Pharmaceutical Excipients" (1986). Suitable excipients include, but are not limited to, ascorbic acid and other antioxidants, chelating agents, such as EDTA, carbohydrates, such as dextran, hydroxyalkylcellulose, hydroxyalkylmethylcellulose, stearic acid and the like. The pH of the pharmaceutical formulations may preferably range from about 3 to about 11, and more preferably from about 7 to about 10.

While it is possible for the active ingredients to be administered alone, it may be preferable to present them as pharmaceutical formulations. The pharmaceutical formulations, both for veterinary and for human use, of the invention comprise at least one active ingredient, as above defined, together with one or more carriers or excipients and optionally additional therapeutic agents.

A therapeutically effective amount or effective dose are used interchangeably herein and are understood to mean the amount of active ingredient required to bring about the desired result. The effective dose of active ingredient depends, at least, on the nature of the condition being treated, toxicity, whether the compound is being used prophylactically (lower doses) or against an active viral infection, the method of delivery, and the pharmaceutical formulation, and can readily be determined by the clinician using conventional dose escalation studies. The effective amount may be about 0.0001 to about 100 mg/kg body weight per day; preferably, from about 0.01 to about 10 mg/kg body weight per day; more preferably, from about 0.01 to about 5 mg/kg body weight per day; and most preferably, from about 0.05 to about 0.5 mg/kg body weight per day. For example, the daily candidate dose for an adult human of approximately 70 kg body weight may range from about 1 mg to about 1000 mg, preferably between about 5 mg and about 500 mg, and may take the form of single or multiple doses.

In another embodiment, the pharmaceutical composition further comprises at least one additional therapeutic agent. The additional therapeutic agent may be another compound of Formula I or any therapeutic agent suitable for use with the Formula I compound. For example, the additional therapeutic agent may be selected from the group consisting of a corticosteroid, an anti-inflammatory signal transduction modulator, a β2-adrenoreceptor agonist bronchodilator, an anticholinergic, a mucolytic agent, hypertonic saline, an agent that inhibits migration of pro-inflammatory cells to the site of infection, and mixtures thereof. The additional therapeutic agent may also include other drugs for treating Orthomyxoviridae virus infections. In other embodiments, the additional therapeutic agent may be viral haemagglutinin inhibitors, viral neuramidase inhibitors, M2 ion channel blockers, Orthomyxoviridae RNA-dependent RNA polymerases inhibitors, sialidases, and other drugs for treating Orthomyxoviridae infections. In still yet another embodiment, the additional therapeutic agent is an interferon, ribavirin, oseltamivir, zanamivir, laninamivir, peramivir, amantadine, rimantadine, CS-8958, favipiravir, AVI-7100, alpha-1 protease inhibitor or DAS181.

In other certain embodiments of the invention, the Orthomyxoviridae infection being treated by the pharmaceutical composition is caused by a Influenza A virus, a Influenza B virus or a Influenza C virus.

The pharmaceutical compositions include those suitable for any administration route appropriate to the condition to be treated. Suitable routes include oral, inhalation, rectal, nasal, topical (including buccal and sublingual), vaginal and parenteral (including subcutaneous, intramuscular, intravenous, intradermal, intrathecal and epidural), and the like. It will be appreciated that the preferred route may vary, for example, with the condition of the recipient.

The pharmaceutical compositions may conveniently be presented in unit dosage form and may be prepared by any method known in the art of pharmacy. Techniques and pharmaceutical compositions generally are found in Remington's Pharmaceutical Sciences (Mack Publishing Co., Easton, Pa.). Such methods include the step of bringing into association the active ingredient with the carrier which constitutes one or more accessory ingredients. In general, the pharmaceutical compositions are prepared by uniformly and intimately bringing into association the active ingredient with liquid carriers or finely divided solid carriers or both, and then, if necessary, shaping the product.

Pharmaceutical compositions of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the pharmaceutical compositions are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical pharmaceutical compositions may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil.

Preferably, a hydrophilic emulsifier is included together with a lipophilic emulsifier, which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream pharmaceutical compositions.

Emulgents and emulsion stabilizers suitable for use in the pharmaceutical composition of the invention include, but are not limited to, Tween® 60, Span® 80, cetostearyl alcohol, benzyl alcohol, myristyl alcohol, glyceryl mono-stearate and sodium lauryl sulfate.

The choice of suitable oils or fats for the pharmaceutical composition is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical compositions according to the present invention comprise a combination according to the invention together with one or more pharmaceutically acceptable carriers or excipients and optionally additional therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Pharmaceutical compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Pharmaceutical compositions for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as *arachis* oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such pharmaceutical compositions may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with a carrier, for example, to produce a single dosage form will vary depending upon the host treated and the particular mode of administration. For example, a time-release pharmaceutical composition intended for oral administration to humans may contain about 1 to about 1000 mg of active ingredient compounded with an appropriate and convenient amount of carrier which may vary from about 5 to about 95% of the total compositions (weight:weight). The pharmaceutical composition can be prepared to provide easily measurable amounts for administration. For example, an aqueous solution intended for intravenous infusion may contain from about 3 to about 500 μg of the active ingredient per milliliter of solution in order to achieve an infusion rate of about 30 mL/hr.

Pharmaceutical compositions suitable for topical administration to the eye also include eye drops wherein the active ingredient is dissolved or suspended in a suitable carrier, especially an aqueous solvent for the active ingredient. The active ingredient is preferably present in such pharmaceutical compositions in a concentration of about 0.5 to about 20% w/w.

Pharmaceutical compositions suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for rectal administration may be presented as a suppository with a suitable base comprising for example cocoa butter or a salicylate.

Pharmaceutical compositions suitable for intrapulmonary or nasal administration have a particle size for example in the range of about 0.1 to about 500 microns, such as about 0.5, about 1, about 30, about 35 etc., which is administered by rapid inhalation through the nasal passage or by inhalation through the mouth so as to reach the alveolar sacs. Suitable pharmaceutical compositions include aqueous or oily solutions of the active ingredient.

Pharmaceutical compositions suitable for aerosol or dry powder administration may be prepared according to conventional methods and may be delivered with additional therapeutic agents such as compounds heretofore used in the treatment or prophylaxis of Orthomyxoviridae infections as described below.

In another aspect, the invention is a novel, efficacious, safe, nonirritating and physiologically compatible inhalable composition comprising a compound of Formula I, II, or a pharmaceutically acceptable salt thereof, suitable for treating Orthomyxoviridae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable pharmaceutical composition is delivered to the endobronchial space in an aerosol comprising particles with a mass median aerodynamic diameter (MMAD) between about 1 and about 5 m. Preferably, the compound of Formula I is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol Medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the pharmaceutical composition for nebulization is delivered to the endobronchial space in an aerosol comprising particles with a MMAD predominantly between about 1 μm and about 5 jpm using a nebulizer able to aerosolize the pharmaceutical composition of the compound of Formula I into particles of the required MMAD. To be optimally therapeutically effective and to avoid upper respiratory and systemic side effects, the majority of aerosolized particles should not have a MMAD greater than about 5 jpm. If an aerosol contains a large number of particles with a MMAD larger than 5 jpm, the particles are deposited in the upper airways decreasing the amount of drug delivered to the site of inflammation and bronchoconstriction in the lower respiratory tract. If the MMAD of the aerosol is smaller than about 1 μm, then the particles have a tendency to remain suspended in the inhaled air and are subsequently exhaled during expiration.

When formulated and delivered according to the method of the invention, the aerosol pharmaceutical composition for nebulization delivers a therapeutically efficacious dose of the compound of Formula I to the site of Orthomyxoviridae infection sufficient to treat the Orthomyxoviridae infection. The amount of drug administered must be adjusted to reflect the efficiency of the delivery of a therapeutically effective dose of the compound of Formula I. In a preferred embodiment, a combination of the aqueous aerosol pharmaceutical composition with the atomizing, jet, pressurized, vibrating porous plate, or ultrasonic nebulizer permits, depending on the nebulizer, about, at least, 20, to about 90%, typically about 70% delivery of the administered dose of the compound of Formula I, II or III into the airways. In a preferred embodiment, at least about 30 to about 50% of the active ingredient is delivered. More preferably, about 70 to about 90% of the active ingredient is delivered.

In another embodiment of the instant invention, a compound of Formula I or a pharmaceutically acceptable salt thereof, is delivered as a dry inhalable powder. The compounds of the invention are administered endobronchially as a dry powder pharmaceutical composition to efficacious deliver fine particles of compound into the endobronchial space using dry powder or metered dose inhalers. For delivery by DPI, the compound of Formula I is processed into particles with, predominantly, MMAD between about 1 m and about 5 μm by milling spray drying, critical fluid processing, or precipitation from solution. Media milling, jet milling and spray-drying devices and procedures capable of producing the particle sizes with a MMAD between about 1 μm and about 5 μm are well know in the art. In one embodiment, excipients are added to the compound of Formula I before processing into particles of the required sizes. In another embodiment, excipients are blended with the particles of the required size to aid in dispersion of the drug particles, for example by using lactose as an excipient.

Particle size determinations are made using devices well known in the art.

For example, a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of Formula I is delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the pharmaceutical composition of the drug into small particles of MMAD from 1 μm and about 5 μm, and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of Formula I, or a pharmaceutically acceptable salt thereof, is delivered as a dry powder using either type of dry powder inhaler as described herein, wherein the MMAD of the dry powder, exclusive of any excipients, is predominantly in the range of about 1 μm to about 5 μm.

In another preferred embodiment, a compound of Formula I is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361,306 and 6,116,234. In preferred embodiments, a compound of Formula I, or a pharmaceutically acceptable salt thereof, is delivered as a dry powder using a metered dose inhaler wherein the MMAD of the dry powder, exclusive of any excipients, is predominantly in the range of about 1 to about 5 ptm.

Pharmaceutical compositions suitable for vaginal administration may be presented as pessaries, tampons, creams, gels, pastes, foams or spray pharmaceutical compositions containing in addition to the active ingredient such carriers as are known in the art to be appropriate.

Pharmaceutical compositions suitable for parenteral administration include aqueous and non-aqueous sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents.

The pharmaceutical compositions are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage pharmaceutical compositions are those containing a daily dose or unit daily sub-dose, as herein above recited, or an appropriate fraction thereof, of the active ingredient.

It should be understood that in addition to the ingredients particularly mentioned above the pharmaceutical compositions of this invention may include other agents conventional in the art having regard to the type of pharmaceutical composition in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention may be used to provide controlled release pharmaceutical formulations containing as an active ingredient one or more compounds of the invention ("controlled release formulations") in which the release of the active ingredient are controlled and regulated to allow less frequency dosing or to improve the pharmacokinetic or toxicity profile of a given active ingredient.

In another embodiment, the present application discloses pharmaceutical compositions comprising a compound of the present invention, or a pharmaceutically acceptable salt, solvate, or ester thereof, in combination with at least one additional therapeutic agent, and a pharmaceutically acceptable carrier or exipient.

For the treatment of Orthomyxoviridae virus infections, preferably, the additional therapeutic agent is active against Orthomyxoviridae virus infections, particularly Influenza virus infections. Non-limiting examples of these active therapeutic agents are viral haemagglutinin inhibitors, viral neuramidase inhibitors, M2 ion channel blockers, Orthomyxoviridae RNA-dependent RNA polymerases inhibitors and sialidases. Non-limiting examples of neuramidase inhibitors include oseltamivir, zanamivir, laninamivir, peramivir and CS-8958. Non-limiting examples of viral M2 channel inhibitors include amantadine and rimantadine. Non-limiting examples of Orthomyxoviridae RNA-dependent RNA polymerases inhibitors are ribavirin and favipiravir. A non-limiting example of sialidases is DAS181. In another embodiment, the additional therapeutic agent is selected from the group consisting of ribavirin, oseltamivir, zanamivir, laninamivir, peramivir, amantadine, rimantadine, CS-8958, favipiravir, AVI-7100, alpha-1 protease inhibitor and DAS181.

Many of the infections of the Orthomyxoviridae viruses are respiratory infections. Therefore, additional active therapeutics used to treat respiratory symptoms and sequelae of infection may be used in combination with the compounds of Formula I, II or III. For example, other preferred additional therapeutic agents in combination with the compounds of Formula I, II or III for the treatment of viral respiratory infections include, but are not limited to, bronchodilators and corticosteroids.

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds of Formula I are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salts thereof.

Other anti-inflamatory agents working through anti-inflamatory cascade mechanisms are also useful as additional therapeutic agents in combination with the compounds of Formula I for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Agents that inhibit migration of pro-inflammatory cells to the site of infection are also useful as additional therapeutic agents in combination with the compounds of Formula I for the treatment of viral respiratory infections. Non-limiting examples of such agents that act through this mechanism and have demonstrated utility in animals by, for example, reducing the eventual mortality caused by influenza are EV-077 (a dual thromboxane synthase inhibitor/thromboxane receptor antagonist) and Fingolimod® (a sphingosine-1-phosphate receptor antagonist).

Combinations comprising inhaled β2-adrenoreceptor agonist bronchodilators such as formoterol, albuterol or salmeterol with the compounds of Formula I are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds of Formula I are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with the compounds of Formula I for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester.

The compounds of Formula I may also be combined with mucolytic agents to treat both the infection and symptoms of respiratory infections. A non-limiting example of a mucolytic agent is ambroxol. Similarly, the compounds of Formula I may be combined with expectorants to treat both the infection and symptoms of respiratory infections. A non-limiting example of an expectorant is guaifenesin.

Nebulized hypertonic saline is used to improve immediate and Ion-term clearance of small airways in patients with lung diseases (Kuzik, *J. Pediatrics* 2007, 266). The compounds of Formula I may also be combined with nebulized hypertonic saline particularly when the Orthomyxoviridae virus infection is complicated with bronchiolitis. The combination of the compounds of Formula I with hypertonic saline may also comprise any of the additional agents discussed above. In a preferred aspect, nebulized about 3% hypertonic saline is used.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents.

Alternatively, a unit dose of one or more additional therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The third embodiment of the present invention is directed to a method for treating an Orthomyxoviridae infection in a mammal in need thereof. The method comprises the step of administering a therapeutically effective amount of a compound of Formula I, as defined above with respect to the first embodiment of the invention. In a certain embodiment thereof, the compound of Formula I is represented by Formula II or Formula III, as defined above with respect to the first embodiment of the invention. Terms in the third embodiment of the invention are defined as above with respect to the first and second embodiments of the invention. Preferred embodiments of $R^1$, $R^2$, $R^3$, $R^{4'}$ $R^5$, $R^6$ and $R^7$ in the third embodiment of the invention are the same as for the first embodiment of the invention.

Preferably the compound of Formula I is:

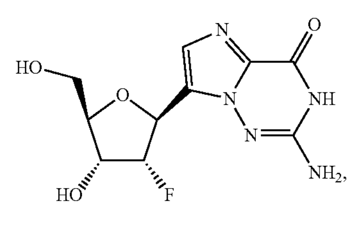

,

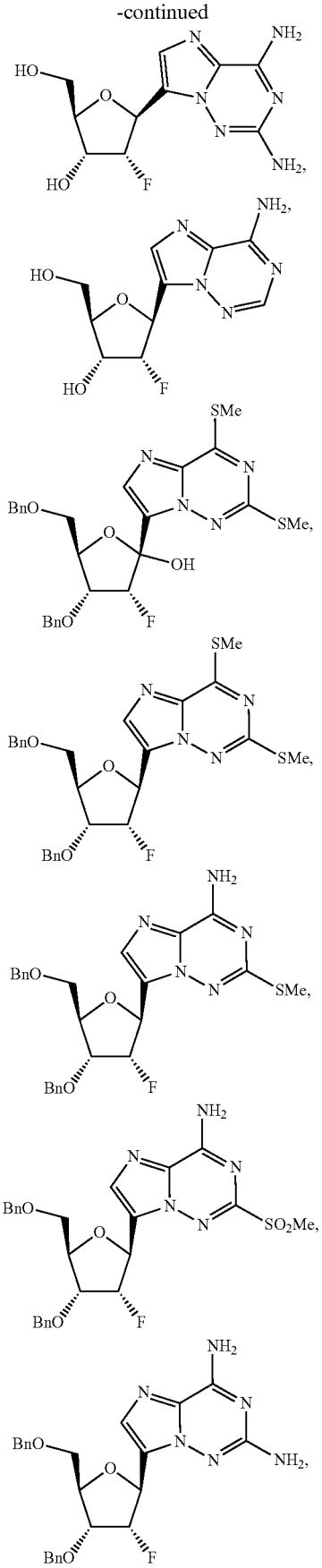
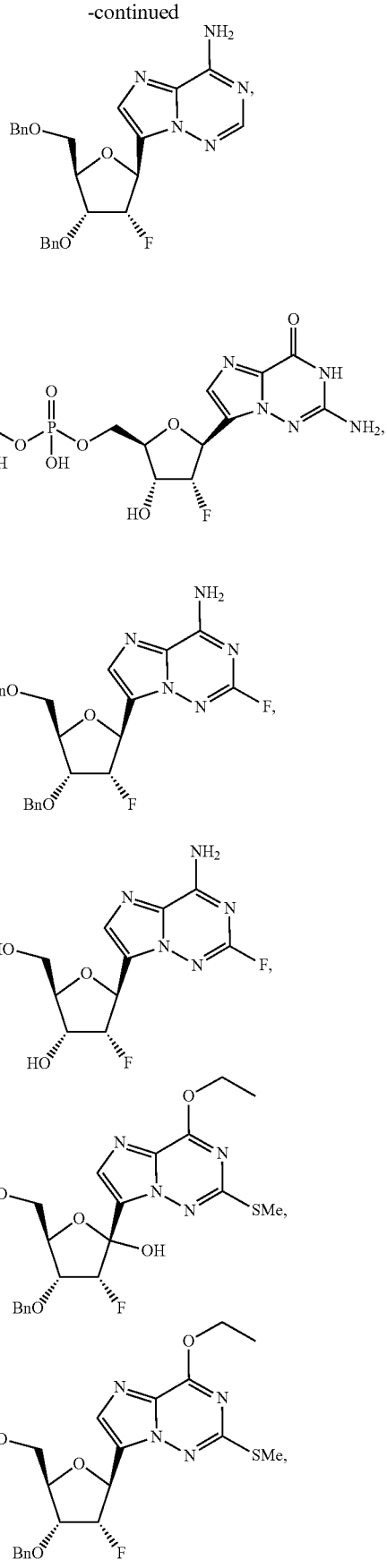

-continued
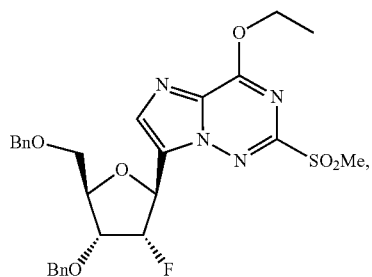
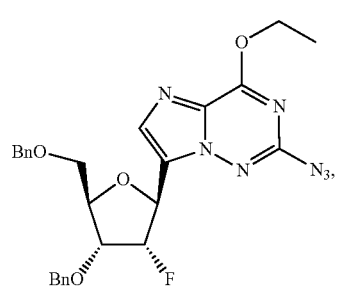
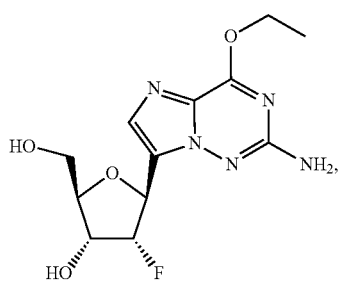
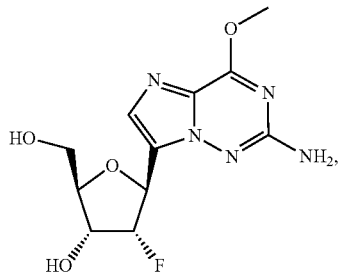
or a pharmaceutically acceptable salt, solvate, or ester thereof, and more preferably is
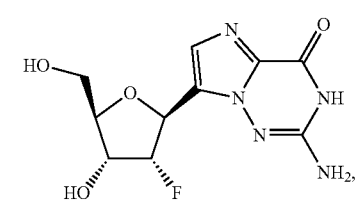
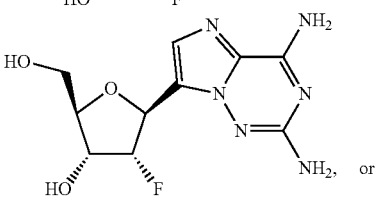
-continued
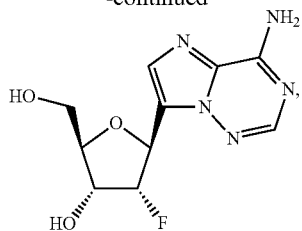
or a pharmaceutically acceptable salt, solvate or ester thereof.
In another preferred embodiment of the invention, the compound of Formula I is:
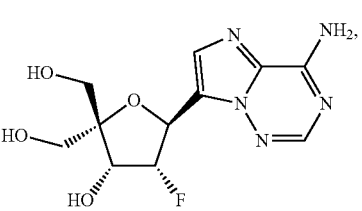
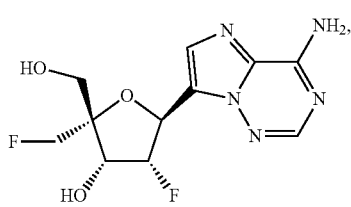
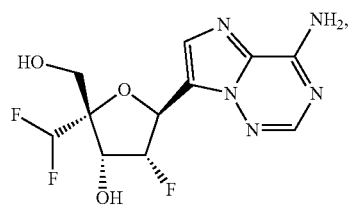
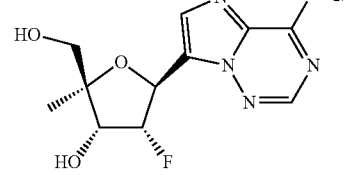
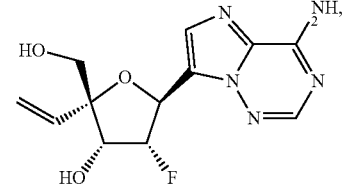
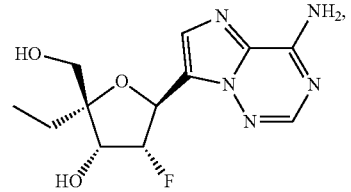

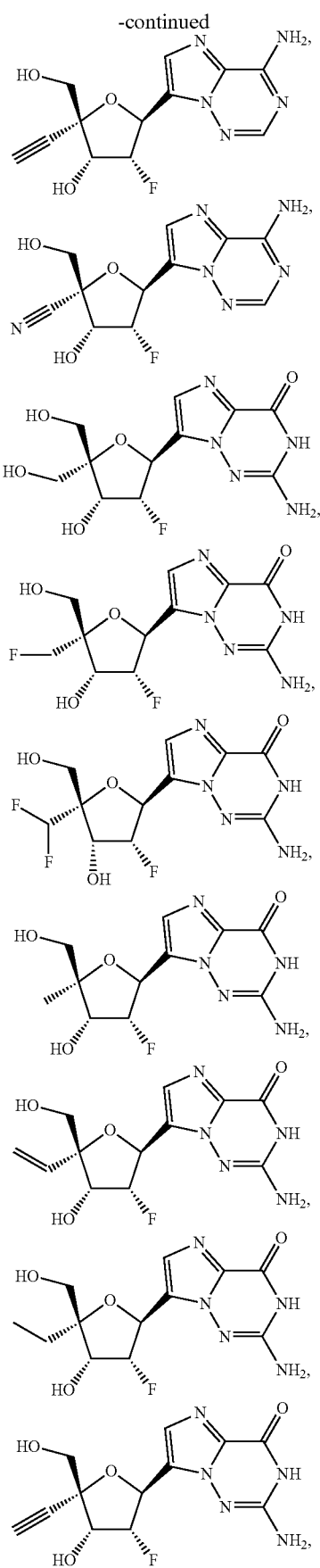
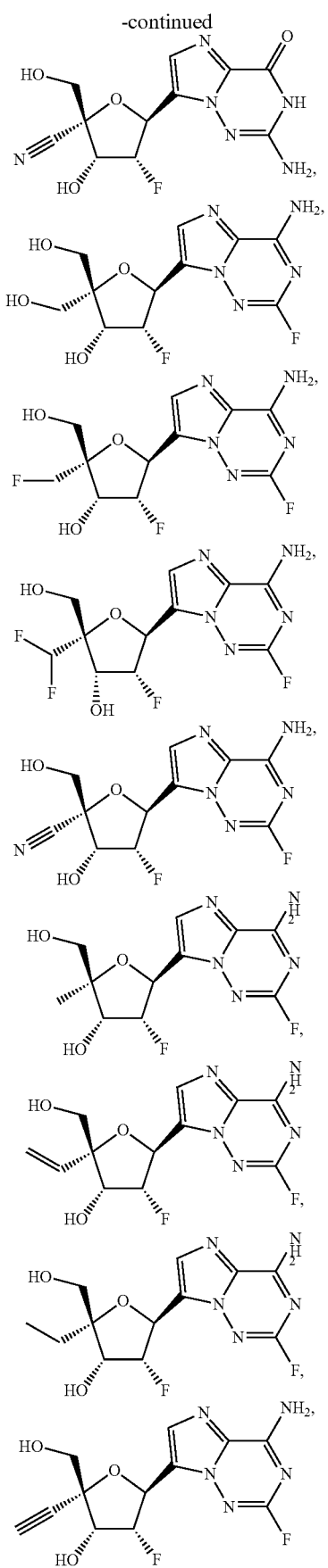

-continued

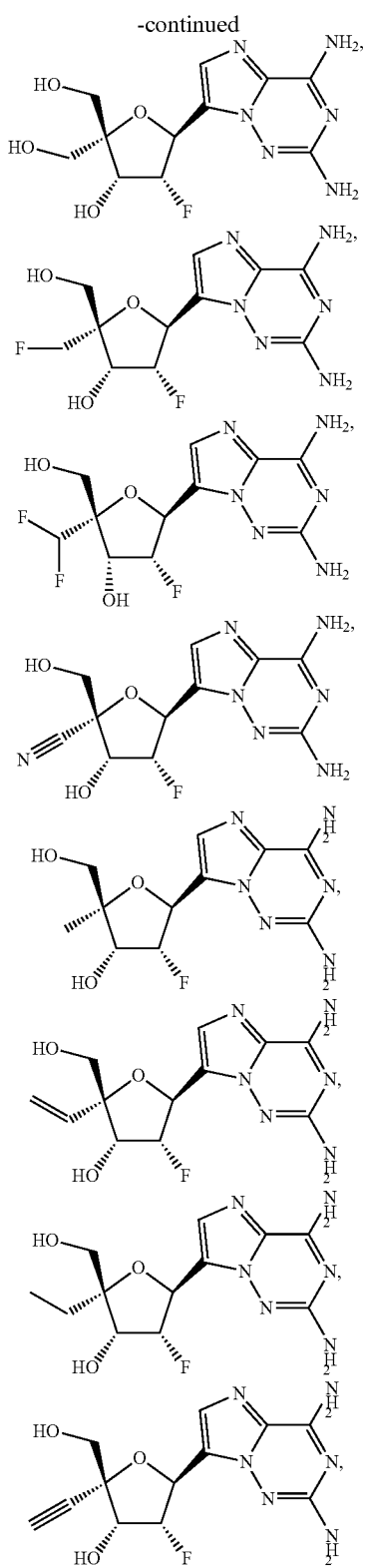

or a pharmaceutically acceptable salt, solvate, or ester thereof.

In another embodiment of the invention, a therapeutically effective amount of a racemate, enantiomer, diastereomer, tautomer, polymorph, pseudopolymorph, amorphous form, or hydrate of a compound of Formula I or a pharmaceutically acceptable salt, solvate or ester thereof is administered to a mammal in need thereof.

In another embodiment, provided is the use of a compound of Formula I or a pharmaceutically acceptable salt, solvate, or ester thereof to treat a viral infection caused by an Orthomyxoviridae virus.

In another aspect of this third embodiment, the Orthomyxoviridae infection being treated is an Influenza virus A infection. In another aspect of this embodiment, the Orthomyxoviridae infection is an Influenza virus B infection. In another aspect of this embodiment, the Orthomyxoviridae infection is an Influenza virus C infection.

In a preferred embodiment, the method of the invention comprises treating an Orthomyxoviridae infection in a mammal in need thereof by administering a therapeutically effective amount of a compound of Formula I or a pharmaceutically acceptable salt or ester thereof.

In another embodiment, the method of the invention comprises treating an Orthomyxoviridae infection in a mammal in need thereof by administering a therapeutically effective amount of a pharmaceutical composition comprising an effective amount of a Formula I compound, or a pharmaceutically acceptable salt, solvate or ester thereof, in combination with a pharmaceutically acceptable diluent or carrier. Any carrier or diluent known in the art for use in pharmaceutical compositions, which is also compatible with the other ingredients of the formulation and physiologically innocuous to the recipient thereof, may be used in the present invention. Suitable diluents include, but are not limited to, calcium or sodium carbonate, lactose, calcium or sodium phosphate.

In another embodiment, the method of the invention comprises treating an Orthomyxoviridae infection in a mammal in need thereof by administering a therapeutically effective amount of a pharmaceutical composition comprising an effective amount of a Formula I compound, or a pharmaceutically acceptable salt or ester thereof, in combination with at least one additional therapeutic agent. The additional therapeutic agent may be any therapeutic agent suitable for use with the Formula I compound. For example, the therapeutic agent may be selected from the group consisting of viral haemagglutinin inhibitors, viral neuramidase inhibitors, M2 ion channel blockers, Orthomyxoviridae RNA-dependent RNA polymerases inhibitors, sialidases, and other drugs for treating Orthomyxoviridae infections.

In still yet another embodiment, the present invention provides for methods of treating Orthomyxoviridae infections in a patient, comprising: administering to the patient a therapeutically effective amount of a compound of Formula I, II, or a pharmaceutically acceptable salt, solvate, or ester thereof.

In still yet another embodiment, the present application provides for methods of treating Orthomyxoviridae infections in a patient, comprising: administering to the patient a therapeutically effective amount of a compound of Formula I, II, or a pharmaceutically acceptable salt, solvate, or ester thereof, and at least one additional active therapeutic agent, whereby Orthomyxoviridae polymerase is inhibited.

In still yet another embodiment, the present application provides for methods of treating Orthomyxoviridae infections in a patient, comprising: administering to the patient a therapeutically effective amount of a compound of Formula I, II, or a pharmaceutically acceptable salt, solvate, or ester thereof, and at least one additional active therapeutic agent selected from the group consisting of interferons, ribavarin analogs, a viral haemagglutinin inhibitor, a viral neuramidase inhibitor, an M2 ion channel blocker, an Orthomyxoviridae RNA-dependent RNA polymerases inhibitor, a sialidase, and other drugs for treating Orthomyxoviridae infections.

In still yet another embodiment, the present application provides for the use of a compound of the present invention, or a pharmaceutically acceptable salt, solvate, and/or ester thereof, for the preparation of a medicament for treating an Orthomyxoviridae infections in a patient.

In another aspect of the invention, processes are disclosed below, which may be used for preparing Formula I compounds of the invention.

Another aspect of the invention relates to methods of inhibiting the activity of Orthomyxoviridae polymerase comprising the step of treating a sample suspected of containing Orthomyxoviridae virus with a composition of the invention.

Compositions of the invention may act as inhibitors of Orthomyxoviridae polymerase, as intermediates for such inhibitors, or have other utilities as described below. The inhibitors will bind to locations on the surface or in a cavity of Orthomyxoviridae polymerase having a geometry unique to Orthomyxoviridae polymerase. Compositions binding Orthomyxoviridae polymerase may bind with varying degrees of reversibility. Those compounds that bind substantially irreversibly are ideal candidates for use in this method of the invention. Once labeled, the substantially irreversibly binding compositions are useful as probes for the detection of Orthomyxoviridae polymerase. Accordingly, the invention relates to methods of detecting Orthomyxoviridae polymerase in a sample suspected of containing Orthomyxoviridae polymerase comprising the steps of: treating a sample suspected of containing Orthomyxoviridae polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing Orthomyxoviridae polymerase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically, the sample will be suspected of containing an organism which produces Orthomyxoviridae polymerase, frequently a pathogenic organism such as Orthomyxoviridae virus. Samples can be contained in any medium including water and organic solvent\water mixtures. Samples include living organisms such as humans, and man made materials such as cell cultures.

The treating step of the invention comprises adding the composition of the invention to the sample or adding a precursor of the composition to the sample. The addition step comprises any method of administration as described herein.

If desired, the activity of Orthomyxoviridae polymerase after application of the composition can be observed by any method including direct and indirect methods of detecting Orthomyxoviridae polymerase activity. Quantitative, qualitative, and semiquantitative methods of determining Orthomyxoviridae polymerase activity are all contemplated. Typically one of the screening methods described above are applied, however, any other method such as observation of the physiological properties of a living organism are also applicable.

Organisms that contain Orthomyxoviridae polymerase include the Orthomyxoviridae virus. The compounds of this invention are useful in the treatment or prophylaxis of Orthomyxoviridae infections in animals or in man.

In still yet another embodiment, the present application provides for methods of inhibiting Orthomyxoviridae RNA-dependent RNA polymerase in a cell, comprising: contacting a cell infected with Orthomyxoviridae virus with an effective amount of a compound of Formula I, II, or a pharmaceutically acceptable salt, solvate, or ester thereof, whereby the Orthomyxoviridae polymerase is inhibited. IN an aspect of this embodiment, the cell is also contacted by at least one additional therapeutic agent. In certain embodiments of the invention, the Orthomyxoviridae RNA-dependent RNA polymerase may be a Influenza virus A RNA-dependent RNA polymerase, a Influenza virus B RNA-dependent RNA polymerase, a Influenza virus C RNA-dependent RNA polymerase, or mixtures thereof.

In still yet another embodiment, the present application provides for methods of inhibiting Orthomyxoviridae polymerase in a cell, comprising: contacting a cell infected with Orthomyxoviridae virus with an effective amount of a compound of Formula I, II, or a pharmaceutically acceptable salt, solvate, or ester thereof, and at least one additional active therapeutic agent selected from the group consisting of interferons, ribavirin analogs, viral neuramidase inhibitors, viral neuramidase inhibitors, M2 ion channel blockers, Orthomyxoviridae RNA-dependent RNA polymerases inhibitors, sialidases and other drugs used to treat Orthomyxoviridae virus infections.

In another aspect, the invention also provides processes and novel intermediates disclosed herein which are useful for preparing Formula I compounds of the invention.

In other aspects, novel methods for synthesis, analysis, separation, isolation, purification, characterization, and testing of the compounds of this invention are provided.

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no Orthomyxoviridae polymerase inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver or other metabolic organ, or within cells in general.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
| --- | --- |
| Bn | Benzyl |
| DMSO | Dimethylsulfoxide |
| DMF | Dimethylformamide |
| MCPBA | meta-chloroperbenzoic acid |
| m/z | mass to charge ratio |
| MS or ms | mass spectrum |
| THF | tetrahydrofuran |
| δ | parts per million referenced to residual non-deuterated solvent peak |

Preparation of Compounds

Compound 1: (2S,3R,4R,5R)-4-(benzyloxy)-5-(benzyloxymethyl)-2-(2,4-bis(methylthio)imidazo[1,2-f][1,2,4]triazin-7-yl)-3-fluorotetrahydrofuran-2-ol To a mixture of 7-bromo-2,4-bis(methylthio)imidazo[1,2-j][1,2,4]triazine (2.5 g, 7.57 mmol) in THF (30 ml) at −78° C. was dropwise added nBuLi (1.6 M in hexane, 6.15 ml, 9.84 mmol). After stirring at −78° C. for 30 minutes, (3R,4R,5R)-4-(benzyloxy)-5-(benzyloxymethyl)-3-fluoro-dihydrofuran-2(3H)-one (2.43 g, 8.33 mmol) in THF (5 ml) was dropwise added. After stirring at −78° C. for 3 hours, the mixture was allowed to warm to room temperature. The mixture was then stirred at room temperature for 30 minutes and then quenched with saturated NH₄Cl. The reaction was extracted with ethyl acetate. The layers were separated and the combined organic layers were washed with brine, dried over Na₂SO₄ and concentrated to provide crude, which was purified by flash column chromatography with ethyl acetate/hexanes to provide the desired compound (2S,3R,4R,5R)-4-(benzyloxy)-5-(benzyloxymethyl)-2-(2,4-bis(methylthio)imidazo[1,2-f][1,2,4]triazin-7-yl)-3-fluorotetrahydrofuran-2-ol (1) (2 g, 48%) as yellow foam. MS (m/z): 543.2 [M+H]⁺.

Compound 2: 7-((2S,3S,4R,5R)-4-(benzyloxy)-5-(benzyloxymethyl)-3-fluorotetrahydrofuran-2-yl)-2,4-bis(methylthio)imidazo[1,2-f][1,2,4]triazine To a solution of (2S,3R,4R,5R)-4-(benzyloxy)-5-(benzyloxymethyl)-2-(2,4-bis(methylthio)imidazo[1,2-f][1,2,4]triazin-7-yl)-3-fluorotetrahydrofuran-2-ol (1) (300 mg, 0.55 mmol) in dichloromethane (3 ml) at −78° C. was added BF₃.OEt₂ (1.20 ml, 8.81 mmol) dropwise, followed by addition of Et₃SiH (1.52 ml, 8.8 1 mmol). The reaction was allowed warm to room temperature and stirred for 2 hours and then quenched with saturated NaHCO₃ and then extracted with dichloromethane. The organic layers were separated, washed with brine, dried over Na₂SO₄ and concentrated to provide crude, which was purified by flash column chromatography with ethyl acetate/hexanes to provide the desired compound 7-((2S,3S,4R,5R)-4-(benzyloxy)-5-(benzyloxymethyl)-3-fluorotetrahydrofuran-2-yl)-2,4-bis(methylthio)imidazo[1,2-f][1,2,4]triazine (2) (218 mg, 75%). MS (m/z): 527.2 [M+H]⁺.

Compound 3: 7-((2S,3S,4R,5R)-4-(benzyloxy)-5-(benzyloxymethyl)-3-fluorotetrahydrofuran-2-yl)-2-(methylthio)imidazo[1,2-f][1,2,4]triazin-4-amine

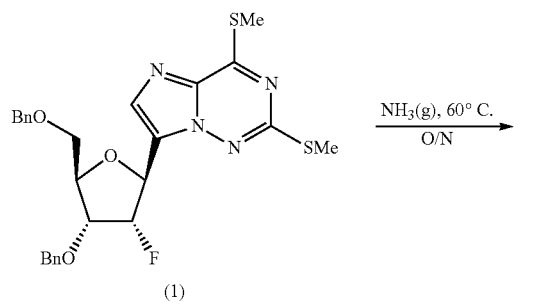
(1)

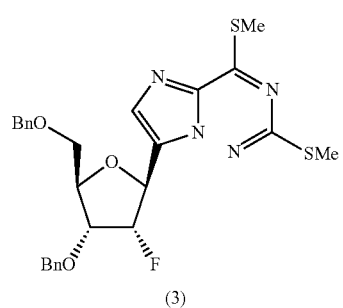
(3)

7-((2S,3S,4R,5R)-4-(benzyloxy)-5-(benzyloxymethyl)-3-fluorotetrahydrofuran-2-yl)-2,4-bis(methylthio)imidazo[1,2-f][1,2,4]triazine (2) (390 mg, 0.74 mmol) in liquid ammonia (120 ml) was heated at 60° C. in a steel bomb for 18 hours. The bomb was cooled down to room temperature and the reaction was purified by flash column chromatography with ethyl acetate/hexanes to provide the desired compound 7-((2S,3S,4R,5R)-4-(benzyloxy)-5-(benzyloxymethyl)-3-fluorotetrahydrofuran-2-yl)-2-(methylthio)imidazo[1,2-f][1,2,4]triazin-4-amine (3) (330 mg, 89%). MS (m/z): 496.2 [M+H]$^+$ Compound 4: 7-((2S,3S,4R,5R)-4-(benzyloxy)-5-(benzyloxymethyl)-3-fluorotetrahydrofuran-2-yl)-2-(methylsulfonyl)imidazo[1,2-Jf][1,2,4]triazin-4-amine

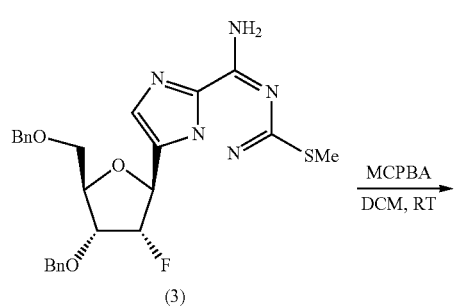
(3)

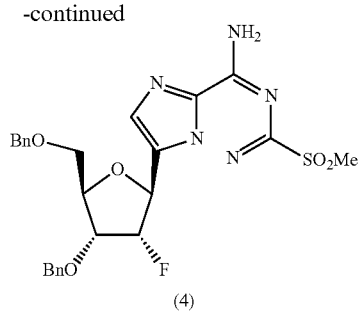
(4)

To a solution of 7-((2S,3S,4R,5R)-4-(benzyloxy)-5-(benzyloxymethyl)-3-fluorotetrahydrofuran-2-yl)-2-(methylthio)imidazo[1,2-f][1,2,4]triazin-4-amine (3) (300 mg, 0.57 mmol) in dichloromethane (10 ml) at 0° C. was added 3-chloroperbenzoic acid (MCPBA, 77%) (627 mg, 3.42 mmol) in one portion. The reaction was allowed to warm to room temperature and stirred for 2 hours. The reaction was quenched with a 20% NaS$_2$O$_3$ solution in H$_2$O (15 ml) and allowed to stir for 20 minutes. The layers were separated, and the aqueous solution was extracted with dichloromethane. The combined organic layers were washed with saturated NaHCO$_3$ and brine, and then dried over Na$_2$SO$_4$ and concentrated to provide a crude mixture which was further purified by silica gel column chromatography with ethyl acetate/dichloromethane to provide the desired product 7-((2S,3S,4R,5R)-4-(benzyloxy)-5-(benzyloxymethyl)-3-fluorotetrahydrofuran-2-yl)-2-(methylsulfonylsulfonyl)imidazo[1,2-f][1,2,4]triazin-4-amine (4) (276 mg, 87%) as clear oil. MS (m/z): 528.1 [M+H]$^+$.

Compound 5: 7-((2S,3S,4R,5R)-4-(benzyloxy)-5-(benzyloxymethyl)-3-fluorotetrahydrofuran-2-yl)imidazo[1,2-f][1,2,4]triazine-2,4-diamine

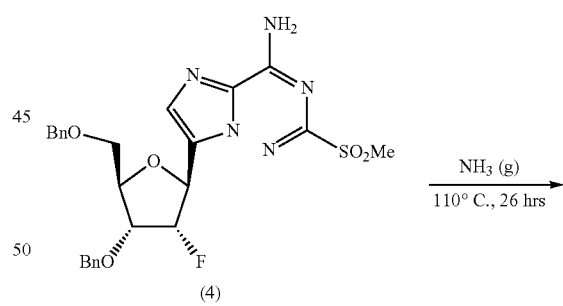

7-((2S,3S,4R,5R)-4-(benzyloxy)-5-(benzyloxymethyl)-3-fluorotetrahydrofuran-2-yl)-2-(methylsulfonyl)imidazo[1,2-f][1,2,4]triazin-4-amine (4) (276 mg, 0.52 mmol) in liquid ammonia (100 ml) was heated at 110° C. for 26 hours in a steel bomb. The bomb was cooled down to room temperature, and the crude reaction was purified by flash column chromatography with ethyl acetate/dichloromethane to provide the desired compound 7-((2S,3S,4R,5R)-4-(benzyloxy)-5-(benzyloxymethyl)-3-fluorotetrahydrofuran-2-yl)imidazo[1,2-f][1,2,4]triazine-2,4-diamine (5) (185 mg, 78%). MS (m/z): 465.3 [M+H]+

Compound 6: (2S,3S,4R,5R)-5-(2,4-diaminoimidazo[1,2-f][1,2,4]triazin-7-yl)-4-fluoro-2-(hydroxymethyl)tetrahydrofuran-3-ol

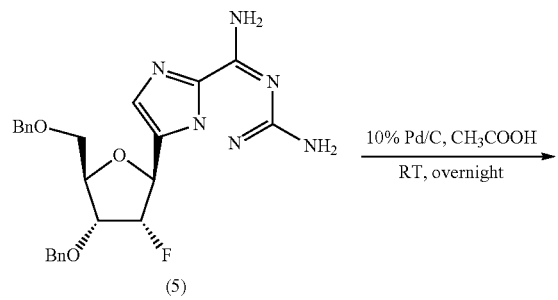

To a solution of 7-((2S,3S,4R,5R)-4-(benzyloxy)-5-(benzyloxymethyl)-3-fluorotetrahydrofuran-2-yl)imidazo[1,2-f][1,2,4]triazine-2,4-diamine (5) (145 mg, 0.31 mmol) in acetic acid (10 ml) was added 10% Pd/C Degussa type E101 NE/W (290 mg). The reaction atmosphere was exchanged for H$_2$ (g) and the reaction stirred for 18 hours. The catalyst was removed by filtration and the mixture concentrated under reduced pressure. The crude was dried to provide the desired product (2S,3S,4R,5R)-5-(2,4-diaminoimidazo[1,2-J][1,2,4]triazin-7-yl)-4-fluoro-2-(hydroxymethyl)tetrahydrofuran-3-ol (6) (85 mg, 96%) as a white solid. MS (m/z): 285.2 [M+H]+.

$^1$H NMR (400 MHz, CD$_3$OD): δ 7.45 (s, 1H), 5.44-5.38 (m, 1H), 5.24-5.11 (d, J=, 1H), 4.38-4.33 (m, 1H), 3.98 (s, 1H), 3.91-3.70 (m 2H).

$^{19}$F (376 MHz, CD$_3$OD): δ (−199.86)-(−200.13) (m)

Compound 7: 2-amino-7-(2S,3S,4R,5R)-3-fluoro-4-hydroxy-5-(hydroxymethyl)tetrahydrofuran-2-yl)imidazo[1,2-f][1,2,4]triazin-4(3H)-one

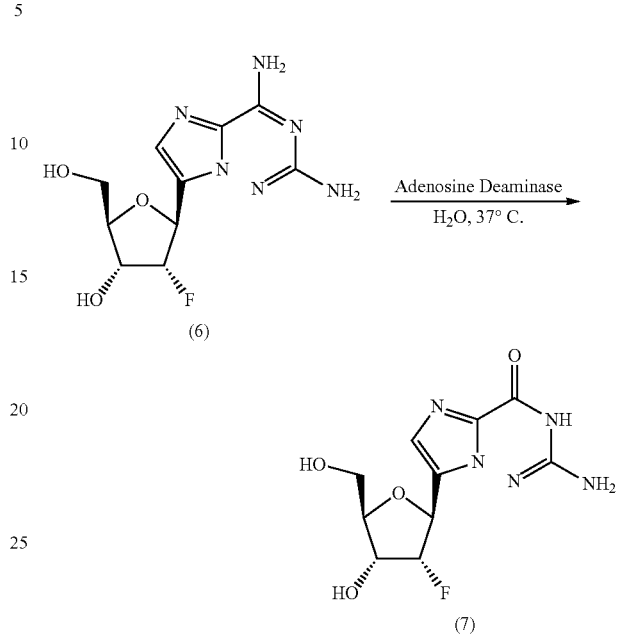

To a solution of (2S,3S,4R,5R)-5-(2,4-diaminoimidazo[1,2-f][1,2,4]triazin-7-yl)-4-fluoro-2-(hydroxymethyl)tetrahydrofuran-3-ol (6) (310 mg, 1.09 mmol) in 800 ml water was added bovine spleen adenosine deaminase type IX (Cas No. 9026-93-1, 205 μL). The solution was placed in a 37° C. water bath for 16 hours. The solution was concentrated and the final compound was crystallized separate from impurities using water as the crystallizing solvent. Solids were collected and dried to provide 2-amino-7-(2S,3S,4R,5R)-3-fluoro-4-hydroxy-5-(hydroxymethyl)tetrahydrofuran-2-yl)imidazo[1,2-f][1,2,4]triazin-4(3H)-one (7) (246 mg, 80%) as a pure, off-white solid. MS (m/z): 286.2 [M+H]+.

$^1$H NMR (400 MHz, DMSO-d$_6$): δ 11.27 (s, 1H), 7.41 (s, 1H), 6.24 (s, 2H), 5.43-5.42 (m, 1H), 5.26-5.20 (d, J=22.8 Hz, 1H), 5.09-4.85 (m, 2H), 4.14-4.09 (m, 1H), 3.77 (s, 1H), 3.69-3.51 (m, 2H).

$^{19}$F (376 MHz, DMSO-d$_6$): δ (−196.68)-(−196.94) (m)

Compound 8: ((2R, 3R, 4R, 5S)-5-(2-amino-4-oxo-3,4-dihydroimidazo[1,2-J][1,2,4]triazin-7-yl)-4-fluoro-3-hydroxy-3-hydroxytetrahydrofuran-2-yl)methyl tetrahydrogen triphosphate

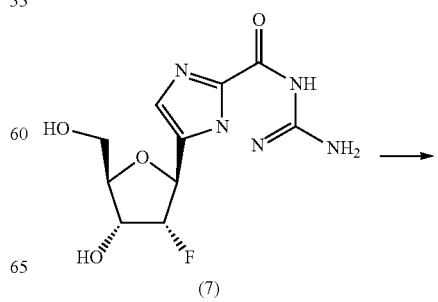

-continued

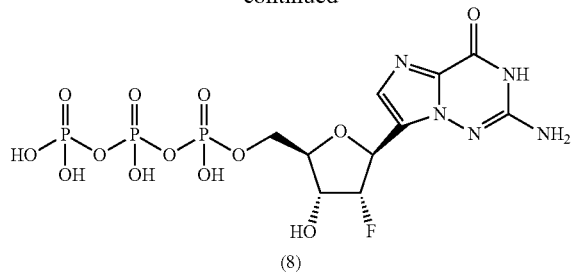

(8)

2-amino-7-(2S,3S,4R,5R)-3-fluoro-4-hydroxy-5-(hydroxymethyl)tetrahydrofuran-2-yl)imidazo[1,2-f][1,2,4]triazin-4(3H)-one (7) (12 mg, 0.042 mmol) was dissolved in trimethylphosphate (1 mL) under an inert atmosphere ($N_2$). Phosphorous oxychloride (58 mg, 0.378 mmol) was added and the mixture was stirred at 0° C. for 2 hours and at room temperature for 2 hours. Monitoring by analytical ion-exchange column determined the time at which >80% of monophosphate was formed. The solution was cooled to 0° C., and a solution of tributylamine (0.15 mL, 0.63 mmol) and triethylammonium pyrophosphate (0.25 g, 0.55 mmol) in anhydrous DMF (1 mL) was added. The reaction mixture was stirred at 0° C. for 2.5 hours and then quenched by the addition of 1N triethylammonium bicarbonate solution in $H_2O$ (6 mL). The mixture was concentrated under reduced pressure and the residue re-dissolved in $H_2O$. The solution was subjected to ion exchange chromatography to yield the desired product ((2R,3R,4R,5S)-5-(2-amino-4-oxo-3,4-dihydroimidazo[1,2-f][1,2,4]triazin-7-yl)-4-fluoro-3-hydroxy-3-hydroxytetrahydrofuran-2-yl)methyl tetrahydrogen triphosphate (8) (as the tetratriethylammonium salt) (11 mg, 28% yield). MS (m/z): 526.0 [M+H]$^+$.

$^1$H NMR (400 MHz, $D_2O$): δ 7.53 (s, 1H), 5.43-5.37 (d, J=24.8 Hz, 1H), 5.29-5.15 (d, J=55.2 Hz, 1H), 4.52-3.47 (m, 4H).

$^{19}$F (376 MHz, $D_2O$): δ (−197.33)-(−197.60) (m, 1F)

$^{31}$P (162 MHz, $D_2O$) δ (−10.66)-(−10.78) (d, J=48.4 Hz, 1P), (−11.070)-(−11.193) (d, J=49.2 Hz, 1P), (−22.990)-(−23.236) (m, 1P).

HPLC ion exchange: Solvent A: Water; Solvent B: 1M triethylammonium bicarbonate.

0-50% over 12 minutes, then 100% for 5 minutes, then back to 0% in 5 minutes.

Column: Dionex, DNAPac PA-100, 4×250 mm.

$T_R$=12.04 min

Compound 9: 7-((2S,3S,4R,5R)-4-(benzyloxy)-5-(benzyloxymethyl)-3-fluorotetrahydrofuran-2-yl)imidazo[1,2-f][1,2,4]triazine-4-amine

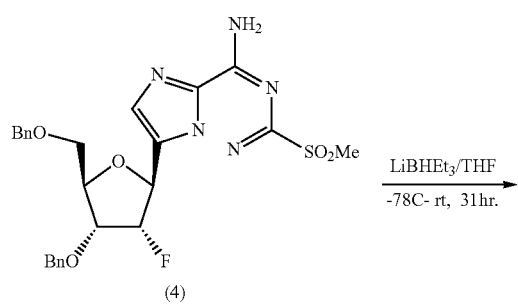

(4)

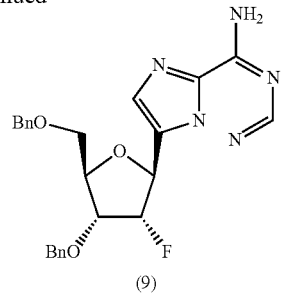

(9)

To a solution of 7-((2S,3S,4R,5R)-4-(benzyloxy)-5-(benzyloxymethyl)-3-fluorotetrahydrofuran-2-yl)-2-(methylsulfonyl)imidazo[1,2-f][1,2,4]triazin-4-amine (4) (63 mg, 0.12 mmol) in THF (5 ml) at −78° C. was added LiBHEt$_3$ (1.0 M in THF, 4.78 ml, 4.78 mmol) drop-wise. The reaction was warmed to room temperature and stirred at room temperature for 31 hours. The reaction mixture was quenched with ice water and extracted with ethyl acetate. The organic solution was washed with brine and concentrated to give a crude mixture which was dissolved in $CH_3OH$ and concentrated in vacuo (3×). The crude was purified by silica gel chromatography with ethyl acetate/dichloromethane to provide the desired product 7-((2S,3S,4R,5R)-4-(benzyloxy)-5-(benzyloxymethyl)-3-fluorotetrahydrofuran-2-yl)imidazo[1,2-f][1,2,4]triazine-4-amine (9) (50 mg, 95% yield). MS (m/z): [M+H]$^+$ 450.3.

Compound 10: (2S,3S,4R,5R)-5-(4-aminoimidazo[1,2-f][1,2,4]triazin-7-yl)-4-fluoro-2-(hydroxymethyl)tetrahydrofuran-3-ol

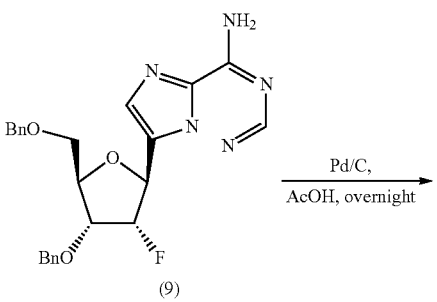

(9)

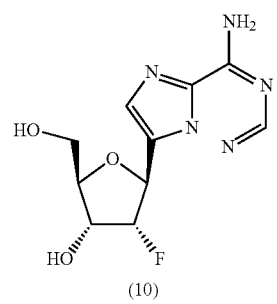

(10)

To a solution of 7-((2S,3S,4R,5R)-4-(benzyloxy)-5-(benzyloxymethyl)-3-fluorotetrahydrofuran-2-yl)imidazo[1,2-f][1,2,4]triazine-4-amine (9) (50 mg, 0.11 mmol) in acetic acid (5 ml) was added 10% Pd/C (100 mg). The reaction vessels atmosphere was exchanged for hydrogen and the reaction was stirred at room temperature overnight. The reaction was filtered through celite and washing with CH₃OH. The filtrate was concentrated to give a crude mixture which was purified by silica gel column chromatography using CH₃OH/dichloromethane to provide the desired product (2S,3S,4R,5R)-5-(4-aminoimidazo[1,2-f][1,2,4]triazin-7-yl)-4-fluoro-2-(hydroxymethyl)tetrahydrofuran-3-ol (10) as a white solid (23 mg, 77% yield). MS (m/z): 270.2 [M+H]⁺.

¹H NMR (400 MHz, DMSO-d₆): δ 8.22 (d, J=26 Hz, 2H), 8.07 (s, 1H), 7.67 (s, 1H), 5.50-5.48 (d, J=6.4, 1H), 5.42-5.36 (m, 1H), 5.19-5.03 (m, 1H), 4.88-4.85 (m, 1H), 4.19-4.11 (m, 1H), 3.83-3.81 (m, 1H), 3.72-3.67 (m, 1H), 3.54-3.50 (m, 1H).

¹⁹F (376 MHz, CD₃OD): δ (−196.69)-(−196.95) (m)

Compound 11: 7-((2S,3S,4R,5R)-4-(benzyloxy)-5-(benzyloxymethyl)-3-fluorotetrahydrofuran-2-yl)-2-fluoroimidazo[1,2-f][1,2,4]triazin-4-amine

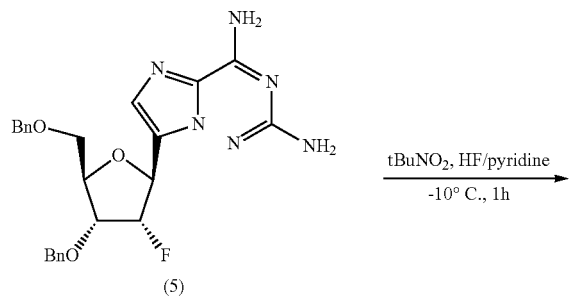

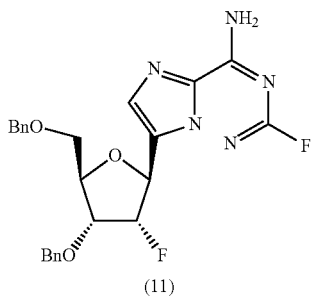

7-((2S,3S,4R,5R)-4-(benzyloxy)-5-(benzyloxymethyl)-3-fluorotetrahydrofuran-2-yl)imidazo[1,2-f][1,2,4]triazine-2,4-diamine (5) (140 mg, 0.30 mmol) in 4 mL 50% HF/pyridine was stirred in a −10° C. bath, and 45 µL (0.38 mmol) t-butyl nitrite was added. The reaction was stirred at low temperature for 1 hour. The reaction was quenched by addition of 50 mL of H₂O and the aqueous layer extracted 2×50 mL dichloromethane. The combined organics were dried over Na₂SO₄ and concentrated. The residue chromatographed on 6 g silica gel to provide the desired compound 7-((2S,3S,4R,5R)-4-(benzyloxy)-5-(benzyloxymethyl)-3-fluorotetrahydrofuran-2-yl)-2-fluoroimidazo[1,2-f][1,2,4]triazin-4-amine (11) (50 mg, 36%). MS (m/z): 468.2 [M+H]⁺.

¹H NMR (400 MHz, CDCl₃): 7.60 (s, 1H), 7.3-7.2 (bm, 10H), 7.14 (bs, 1H), 6.37 (bs, 1H), 5.46-5.48 (dd, J=23.2, 2.4 Hz, 1H), 5.29-5.15 (m, 1H), 4.72 (m, 1H), 4.56-4.52 (m, 2H), 4.29 (m, 2H), 3.83-3.81 (m, 1H), 3.65-3.63 (m, 1H).

¹⁹F (376 MHz, CDCl₃): δ −69.1 (s), (−197.7)-(−198.0) (m).

Compound 12: (2R,3R,4R,5S)-5-(4-amino-2-fluoroimidazo[1,2-f][1,2,4]triazin-7-yl)-4-fluoro-2-(hydroxymethyl)tetrahydrofuran-3-ol

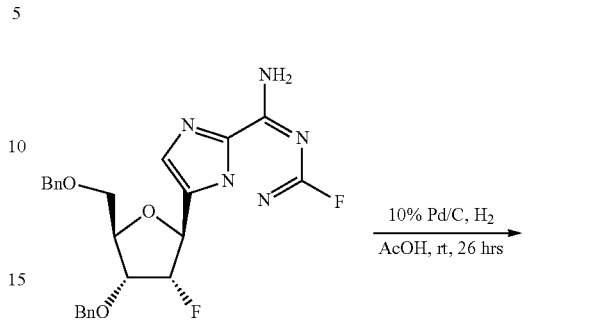

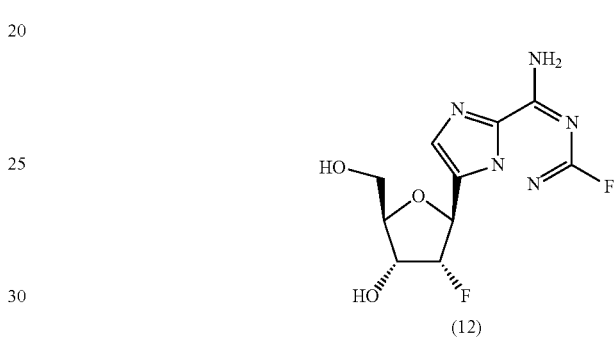

To a solution of 7-((2S,3S,4R,5R)-4-(benzyloxy)-5-(benzyloxymethyl)-3-fluorotetrahydrofuran-2-yl)imidazo[1,2-f][1,2,4]triazine-4-amine (11) (50 mg, 0.11 mmol) in acetic acid (8 ml), 10% Pd/C (100 mg) was added. The reaction vessel's atmosphere was exchanged for hydrogen and the reaction was stirred at room temperature overnight. The reaction was filtered through celite and washed with acetic acid and then CH₃OH. The filtrate was concentrated to give a crude mixture that was purified by reversed phase HPLC to provide the desired product (2R,3R,4R,5S)-5-(4-amino-2-fluoroimidazo[1,2-f][1,2,4]triazin-7-yl)-4-fluoro-2-(hydroxymethyl)tetrahydrofuran-3-ol (12) as a white solid (26 mg, 84%). MS (m/z): 288.1 [M+H]⁺.

¹H NMR (400 MHz, CD₃OD): δ 7.66 (s, 1H), 5.47-5.41 (dd, J=23.6, 2.4 Hz, 1H), 5.21-5.06 (m, 1H), 4.35-4.27 (m, 1H), 3.93 (bm, 1H), 3.88 (m, 1H), 3.68 (m, 1H).

¹⁹F (376 MHz, CD₃OD): δ −72.15 (s), (−199.39)-(−196.69) (m)

Compound 13: 7-bromo-4-ethoxy-2-(methylthio)imidazo[1,2-f][1,2,4]triazine

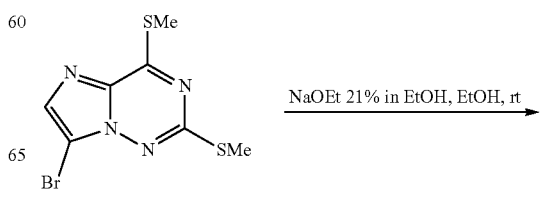

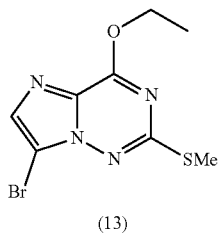

(13)

To a mixture of 7-bromo-2,4-bis(methylthio)imidazo[1,2-f][1,2,4]triazine (1.0 g, 3.45 mmol) in EtOH (25 ml) at room temperature, NaOEt (21% in EtOH, 1.28 ml, 3.45 mmol) was added. After stirring at room temperature for 1 hour, the reaction was quenched with AcOH (1 mL). The solvents were removed under reduced pressure, and the mixture was partitioned between $CH_2Cl_2$ and ½ saturated brine. The organics were separated, dried over $Na_2SO_4$, solids removed by filtration and the solvent removed under reduced pressure. The crude material was purified by flash column chromatography with ethyl acetate/hexanes to provide the desired compound 7-bromo-4-ethoxy-2-(methylthio)imidazo[1,2-f][1,2,4]triazine (13) (791 mg, 79%) as a yellow foam. MS (m/z): 288.9/290.8 $[M+H]^+$.

Compound 14: (2S,3R,4R,5R)-4-(benzyloxy)-5-(benzyloxymethyl)-2-(4-ethoxy-2-(methylthio)imidazo[1,2-f][1,2,4]triazin-7-yl)-3-fluorotetrahydrofuran-2-ol

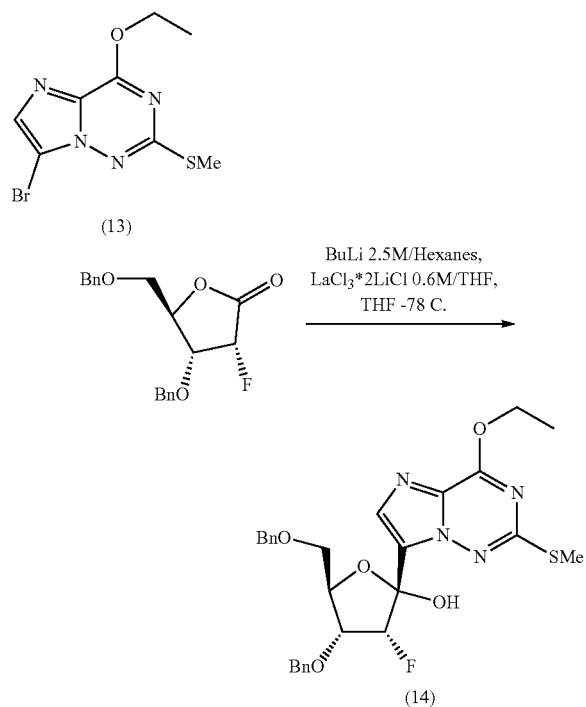

To a mixture of 7-bromo-4-ethoxy-2-(methylthio)imidazo[1,2-f][1,2,4]triazine (13) (917 mg, 3.17 mmol) in THF (15 ml) at −78° C. was added $LaCl_3*2LiCl$ (0.6M in THF, 5.28 mL, 3.17 mmol) followed by the dropwise addition of nBuLi (2.5 M in hexane, 1.27 ml, 3.17 mmol). After stirring at −78° C. for 30 minutes, (3R,4R,5R)-4-(benzyloxy)-5-(benzyloxymethyl)-3-fluorodihydrofuran-2(3H)-one (805 mg, 2.44 mmol) in THF (10 ml) was dropwise added. After, stirring at −78° C. for 30 min and allowing the mixture to warm to room temperature, the mixture was stirred at room temperature for 30 minutes and then quenched with AcOH. The reaction was extracted with ethyl acetate. The layers were separated, and the combined organic layers were washed with brine, dried over $Na_2SO_4$ and concentrated to provide crude, which was purified by flash column chromatography with ethyl acetate/hexanes, to provide the desired compound (2S,3R,4R,5R)-4-(benzyloxy)-5-(benzyloxymethyl)-2-(4-ethoxy-2-(methylthio)imidazo[1,2-f][1,2,4]triazin-7-yl)-3-fluorotetrahydrofuran-2-ol (14) (244 mg, 19%) as yellow foam. MS (m/z): 541.1 $[M+H]^+$.

Compound 15: 7-((2S,3S,4R,5R)-4-(benzyloxy)-5-(benzyloxymethyl)-3-fluorotetrahydrofuran-2-yl)-4-ethoxy-2-(methylthio)imidazo[1,2-f][1,2,4]triazine

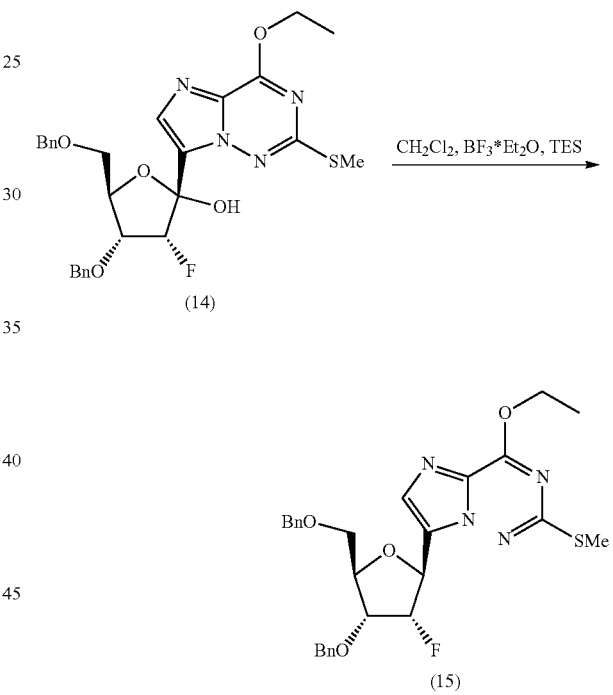

To a solution of (2S,3R,4R, SR)-4-(benzyloxy)-5-(benzyloxymethyl)-2-(4-ethoxy-2-(methylthio)imidazo[1,2-f][1,2,4]triazin-7-yl)-3-fluorotetrahydrofuran-2-ol (X) (244 mg, 0.45 mmol) in $CH_2Cl_2$ (5 ml) at 0° C. was added $BF_3.OEt_2$ (900 µl, 3.5 mmol) drop-wise, followed by addition of $Et_3SiH$ (600 µl, 3.5 mmol). The reaction was allowed to warm to room temperature and stirred for 3 hours. The reaction was quenched with saturated $NaHCO_3$ and extracted with $CH_2Cl_2$. The organic layers were separated, washed with brine, dried over $Na_2SO_4$ and concentrated to give crude, which was purified by flash column chromatography with ethyl acetate/hexanes, to provide the desired compound 7-((2S,3S,4R,5R)-4-(benzyloxy)-5-(benzyloxymethyl)-3-fluorotetrahydrofuran-2-yl)-4-ethoxy-2-(methylthio)imidazo[1,2-f][1,2,4]triazine (15) (107 mg, 46%). MS (m/z): 525.1 $[M+H]^+$.

Compound 16: 7-((2S,3S,4R,5R)-4-(benzyloxy)-5-(benzyloxymethyl)-3-fluorotetrahydrofuran-2-yl)-4-ethoxy-2-(methylsulfonyl)imidazo[1,2-f][1,2,4]triazine

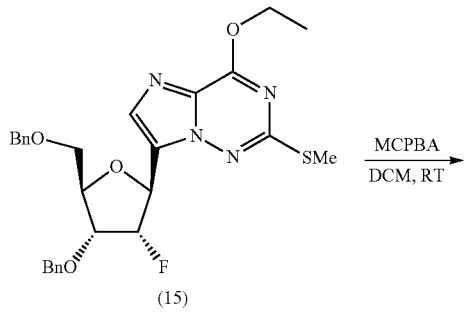

(15)

MCPBA
——————→
DCM, RT (16)

To a solution of 7-((2S,3S,4R,5R)-4-(benzyloxy)-5-(benzyloxymethyl)-3-fluorotetrahydrofuran-2-yl)-4-ethoxy-2-(methylthio)imidazo[1,2-f][1,2,4]triazin (15) (107 mg, 0.204 mmol) in CH$_2$Cl$_2$ (3 ml) at room temperature was added 3-chloroperbenzoic acid (MCPBA, 77%) (100 mg, 0.443 mmol) in one portion. The reaction was stirred at room temperature for 4 hours. The reaction was quenched with a 20% NaS$_2$O$_3$ solution in H$_2$O (5 ml) and allowed to stir for 20 minutes. The layers were separated and the aqueous solution was extracted with CH$_2$Cl$_2$. The combined organic layers were washed with saturated NaHCO$_3$, brine, dried over Na$_2$SO$_4$ and concentrated to provide crude 7-((2S,3S,4R,5R)-4-(benzyloxy)-5-(benzyloxymethyl)-3-fluorotetrahydrofuran-2-yl)-4-ethoxy-2-(methylsulfonyl)imidazo[1,2-f][1,2,4]triazine (16), which was carried forward without purification. MS (m/z): 557.1 [M+H]$^+$.

Compound 17: 2-azido-7-((2S,3S,4R,5R)-4-(benzyloxy)-5-(benzyloxymethyl)-3-fluorotetrahydrofuran-2-yl)-4-ethoxyimidazo[1,2-f][1,2,4]triazine (16)

NaN$_3$, DMSO, rt
——————→

(17)

To a solution of NaN$_3$ (66 mgs, 1.01 mmol) in DMSO (5 mL) was added 7-((2S,3S,4R,5R)-4-(benzyloxy)-5-(benzyloxymethyl)-3-fluorotetrahydrofuran-2-yl)-4-ethoxy-2-(methylsulfonyl)imidazo[1,2-f][1,2,4]triazine (16) (113 mgs, 0.203 mmol) in one portion. The reaction was allowed to stir at room temperature for 16 hours. The mixture was partitioned between EtOAc/H$_2$O. The organics were separated and dried over Na$_2$SO$_4$, and purified by silica gel chromatography with EtOAc/hexanes to provide 2-azido-7-((2S,3S,4R,5R)-4-(benzyloxy)-5-(benzyloxymethyl)-3-fluorotetrahydrofuran-2-yl)-4-ethoxyimidazo[1,2-f][1,2,4]triazine (17) (93 mgs, 88%) as an off-white solid. MS (m/z): 520.05 [M+H]$^+$.

Compound 18: (2R,3R,4R,5S)-5-(2-amino-4-ethoxyimidazo[1,2-f][1,2,4]triazine-7-yl)-4-fluoro-2-(hydroxymethyl)tetrahydrofuran-3-ol (17)

MeOH, 10% Pd/C
——————→

(18)

A solution of 2-azido-7-((2S,3S,4R,5R)-4-(benzyloxy)-5-(benzyloxymethyl)-3-fluorotetrahydrofuran-2-yl)-4-ethoxyimidazo[1,2-f][1,2,4]triazine (17) (93 mg, 0.18 mmol) in CH$_3$OH (5 mL) was purged with argon, and 10% Pd/C (100 mg) was added. The reaction vessel was evacuated and back filled with H$_2$ three times. The reaction mixture was then allowed to stir under a hydrogen atmosphere for 16 hours. The solids were filtered off, and the organics were removed under reduced pressure to give crude material that was purified by HPLC to give (2R,3R,4R,5S)-5-(2-amino-4-ethoxyimidazo[1,2-f][1,2,4]triazine-7-yl)-4-fluoro-2-(hydroxymethyl)tetrahydrofuran-3-ol (18) (27 mg, 48%) as a white solid. MS (m/z): 314.10 [M+H]$^+$.

$^1$H NMR (400 MHz, DMSO-d$_6$): δ 7.526 (s, 1H), 8.07 (s, 1H), 6.55 (s, 2H), 5.43-5.41 (d, J=6.46 Hz, 1H), 5.33-5.27 (dd, J=2.25 and 22.69 Hz, 1H), 5.11-4.96 (m, 1H), 4.84 (t, J=5.58 Hz, 1H), 4.52-4.47 (q, J=7.04 Hz, 2H), 4.17-4.07 (m, 1H), 3.78-3.76 (m, 1H), 3.69-3.65 (m, 1H), 3.511-3.45 (m, 1H), 1.37 (t, J=7.04 Hz, 3H).

$^{19}$F (376 MHz, DMSO-d$_6$): δ (−196.79)-(−197.05) (m)

Compound 19: (2R,3R,4R,5S)-5-(2-amino-4-methoxyimidazo[1,2-f][1,2,4]triazin-7-yl)-4-fluoro-2-(hydroxymethyl)tetrahydrofuran-3-ol

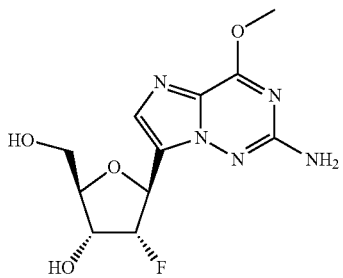

(19)

(2R,3R,4R,5S)-5-(2-amino-4-methoxyimidazo[1,2-f][1,2,4]triazin-7-yl)-4-fluoro-2-(hydroxymethyl)tetrahydrofuran-3-ol (19) was prepared in a directly analogous manner as that used for the preparation of (2R,3R,4R,5S)-5-(2-amino-4-ethoxyimidazo[1,2-f][1,2,4]triazine-7-yl)-4-fluoro-2-(hydroxymethyl)tetrahydrofuran-3-ol, except NaOMe in MeOH was used instead of NaOEt in EtOH in the first step of the synthesis. MS (m/z): 300.18 [M+H]$^+$.

$^1$H NMR (400 MHz, CD$_3$OD): δ 7.56 (s, 1H), 5.46 (dd, J=24, 2.4 Hz, 1H), 5.15 (ddd, J=54.8, 4.4, 2.4 Hz, 1H), 4.34 (ddd, J=4.4, 8, 20.4 Hz, 1H), 4.15 (s, 3H), 3.97 (m, 1H), 3.91 (dd, J=2.4, 12.4 Hz, 1H), 3.72 (dd, J=4.4, 12 Hz, 1H).

$^{19}$F (376 MHz, CD$_3$OD): δ (−198.98)-(−199.25) (m).

Anti-influenza Assays

Influenza RNA Polymerase Inhibition (IC50) Assay

Influenza A/PR/8/34 (H1N1) purified virus was obtained from Advanced Biotechnologies Inc. (Columbia, Md.) as suspension in PBS buffer. Virions were disrupted by exposure to an equal volume of 2% Triton X-100 for 30 minutes at room temperature in a buffer containing 100 mM Tris-HCl, pH 8, 200 mM KCl, 3 mM dithiothreitol [DTT], 10% glycerol, 10 mM MgCl$_2$, 2 U/mL RNasin Ribonuclease Inhibitor, and 2 mg/mL Lysolechithin type V (Sigma, Saint Louis, Mo.). The virus lysate was stored at −80° C. in aliquots.

The concentrations refer to final concentrations unless mentioned otherwise. Nucleotide analog inhibitors were serially diluted 3 fold in water and added to reaction mix containing 10% virus lysate (v/v), 100 mM Tris-HCl (pH 8.0), 100 mM KCl, 1 mM DTT, 10% glycerol, 0.25% Triton-101 (reduced), 5 mM MgCl$_2$, 0.4 U/mL RNasin, and 200 μM ApG dinucleotide primer (TriLink, San Diego Calif.). Reactions were initiated by addition of ribonucleotide triphosphate (NTP) substrate mix containing one α-$^{33}$P labeled NTP and 100 μM of the other three natural NTPs (PerkinElmer, Shelton, Conn.). The radiolabel used for each assay matched the class of nucleotide analog screened. The concentrations for the limiting natural NTP are 20, 10, 2, and 1 μM for ATP, CTP, UTP, and GTP respectively. The molar ratio of un-radiolabeled: radiolabeled NTP were in the range of 100-400:1.

Reactions were incubated at 30° C. for 90 minutes then spotted onto DE81 filter paper. Filters were air dried, washed 0.125 M Na$_2$HPO$_4$ (3×), water (1×), and EtOH (1×), and air dried before exposed to Typhoon phosphor imager and radioactivity was quantified on a Typhoon Trio (GE Healthcare, Piscataway N.J.). IC$_{50}$ values were calculated for inhibitors by fitting the data in GraphPad Prism with a sigmoidal dose response with variable slope equation, fixing the Ymax and Ymin values at 100% and 0%. The IC$_{50}$ for ((2R,3R,4R,5S)-5-(2-amino-4-oxo-3,4-dihydroimidazo[1,2-f][1,2,4]triazin-7-yl)-4-fluoro-3-hydroxy-3-hydroxytetrahydrofuran-2-yl)methyl tetrahydrogen triphosphate (Compound 8) was determined to be 2.8 μM.

Normal Human Bronchial/Tracheal Epithelial Cell Influenza Infection Assay (EC$_{50}$)

Normal Human Bronchial/Tracheal Epithelial Cells (Lonza, Basel Switzerland) are seeded to 384-well plates at a density of 4000 cells per well in BEGM medium supplemented with growth factors (Lonza, Basel Switzerland). Medium is removed next day, and cells are washed three times with 100 μL of RPMI+1% BSA (RPMI-BSA). 30 μL of RPMI-BSA is added to cells thereafter. Compounds are 3-fold serially diluted in DMSO, and 0.4 μL of compound dilutions are stamped to plates. Influenza A virus HK/8/68 (Advanced Biotechnology Inc, Columbia, Md., 13.5 MOI), PC/1/73 (ATCC Manassas, Va., 0.3 MOI) and Influenza B virus B/Lee/40 ((ATCC Manassas, Va., 10 MOI) are added to cells in 10 μL of RPMI-BSA medium supplemented with 8 ug/mL trypsin (Worthington, Lakewood, N.J.). After a five day incubation, 40 μL of buffer containing 66 mM Mes pH 6.5, 8 mM CaCl$_2$, 0.5% NP-40 and 100 μM neuramidase substrate (2'-(4-Methylumbelliferyl)-α-D-N-acetylneuraminic acid sodium salt hydrate, Sigma Aldrich, St. Luis, Mo.) is added to cells. Fluorescence of the product of hydrolysis is read using excitation at 360 nm and emission at 450 nm after a 1 hour incubation at 37° C. EC$_{50}$ values are calculated by non-linear regression of multiple data sets.

The following table summarizes EC$_{50}$s determined by this assay:

| Compound | Infl A PC/1/73 EC$_{50}$ | Infl B Lee/40 EC$_{50}$ |
|---|---|---|
| 19 | 30 μM | 36 μM |
| 18 | >200 μM | >200 μM |
| 12 | >100 μM | >100 μM |
| 10 | 0.9 μM | 0.9 μM |
| 7 | 27 μM | 37 μM |
| 6 | 21 μM | 51 μM |

While the invention has been described with reference to various specific and preferred embodiments and techniques, it will be understood that they are not intended to limit the invention to those embodiments. One skilled in the art will understand that many variations and modifications may be made while remaining within the spirit and scope of the invention. The invention is intended to cover all alternatives, modifications, and equivalents, which may be included within the scope of the present invention.

What is claimed is:

1. A compound of Formula I:

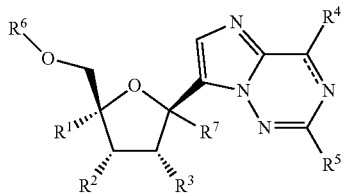

Formula I or a pharmaceutically acceptable salt, solvate, or ester thereof;

wherein:

$R^1$ is H, halogen, $OR^a$, $(C_1\text{-}C_8)$haloalkyl, CN, $N_3$, $(C_1\text{-}C_8)$alkyl, $(C_1\text{-}C_8)$substituted alkyl, $(C_2\text{-}C_8)$alkenyl, $(C_2\text{-}C_8)$substituted alkenyl, $(C_2\text{-}C_8)$alkynyl or $(C_2\text{-}C_8)$ substituted alkynyl, wherein the substituent is selected from the group consisting of —X, —$R^b$, —OH, =O, —$OR^b$, —$SR^b$, —$S^-$, —$NR^b{}_2$, —$N^+R^b{}_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b{}_2$, —S(=O)$_2$—, —S(=O)$_2$OH, —S(=O)$_2R^b$, —OS(=O)$_2$ $R^b$, —S(=O)$_2NR^b{}_2$, —S(=O)$R^b$, —OP(=O)(OR$^b$, —P(=O)(OR$^b$)$_2$, —P(=O)(O$^-$)$_2$, —P(=O)(OH)$_2$, —P(O)(OR$^b$)(O$^-$), —C(=O)$R^b$, —C(=O)X, —C(S)$R^b$, —C(O)OR$^b$, —C(O)O$^-$, —C(S)OR$^b$, —C(O)SR$^b$, —C(S)SR$^b$, —C(O)NR$^b{}_2$, —C(S)NR$^b{}_2$, and —C(=NR$^b$)NR$^b{}_2$, where each X is independently a halogen: F, Cl, Br, or I; and each $R^b$ is independently H, alkyl, aryl, arylalkyl, a heterocycle, or a protecting group or prodrug moiety;

$R^2$ is $OR^a$;

$R^3$ is halogen or $N_3$;

each $R^a$ is independently H, aryl, arylalkyl, or $(C_1\text{-}C_8)$ alkyl;

$R^4$ is H, =O, or $N_3$;

$R^5$ is H, $OR^a$, $N(R^a)_2$, $N_3$, CN, $S(O)_nR^a$, halogen, or $(C_1\text{-}C_8)$haloalkyl;

each n is 0, 1 or 2;

$R^6$ is H, aryl, arylalkyl, or

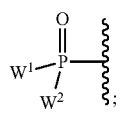

wherein $W^1$ and $W^2$ are each, independently, $OR^a$ or a group of the Formula Ia:

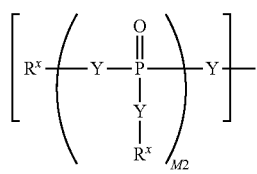

Formula Ia wherein:
each Y is independently a bond or O;
M2 is 0, 1 or 2;
each $R^x$ is H, halogen or OH; and
$R^7$ is H.

2. The compound of claim 1, represented by Formula II:

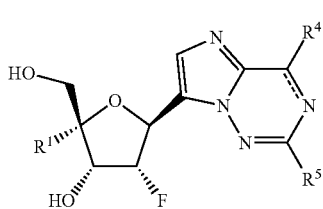

Formula II or a pharmaceutically acceptable salt, solvate, or ester thereof.

3. The compound of claim 2, wherein $R^1$ is H, or a pharmaceutically acceptable salt, solvate, or ester thereof.

4. The compound of claim 1, wherein $R^1$ is H, CH$_2$OH, CH$_2$F, CHF$_2$, CH=CH$_2$, C≡CH, CN, CH$_2$CH=CH$_2$, N$_3$, CH$_3$, or CH$_2$CH$_3$, or a pharmaceutically acceptable salt, solvate, or ester thereof.

5. The compound of claim 4, wherein $R^1$ is H, $R^2$ is OH or O-benzyl, or a pharmaceutically acceptable salt, solvate, or ester thereof.

6. The compound of claim 1, wherein $R^2$ is OH or O-benzyl, or a pharmaceutically acceptable salt, solvate, or ester thereof.

7. The compound of claim 6, wherein $R^2$ is OH, or a pharmaceutically acceptable salt, solvate, or ester thereof.

8. The compound of claim 1, wherein $R^3$ is F or N$_3$, or a pharmaceutically acceptable salt, solvate, or ester thereof.

9. The compound of claim 8, wherein $R^3$ is F, or a pharmaceutically acceptable salt, solvate, or ester thereof.

10. The compound of claim 1, wherein $R^5$ is NH$_2$ and $R^4$ is =O, or a pharmaceutically acceptable salt, solvate, or ester thereof.

11. The compound of claim 1, wherein $R^4$ is H or =O; and $R^5$ is selected from the group consisting of H, NH$_2$, NHMe, NHcPr, OH, OMe, Cl, Br, I, SMe, F, N$_3$, CN, CF$_3$, and SO$_2$Me, or a pharmaceutically acceptable salt, solvate, or ester thereof.

12. The compound of claim 11, wherein $R^4$ is =O, $R^5$ is H or NH$_2$, or a combination thereof, or a pharmaceutically acceptable salt, solvate, or ester thereof.

13. The compound of claim 1, wherein $R^6$ is H, benzyl, or

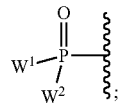

wherein $W^2$ is OH and $W^1$ is a group of the Formula Ia:

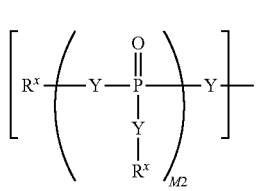

Formula Ia wherein:
Y is O;
M2 is 2; and
each $R^x$ is H,
or a pharmaceutically acceptable salt, solvate, or ester thereof.

14. The compound of claim 13, wherein $R^6$ is H, or a pharmaceutically acceptable salt, solvate, or ester thereof.

15. The compound of claim 1, wherein $R^1$ is H, $R^2$ is OH and $R^3$ is F, or a pharmaceutically acceptable salt, solvate, or ester thereof.

16. The compound of claim 1, or a pharmaceutically acceptable salt thereof.

17. The compound of claim 2, or a pharmaceutically acceptable salt thereof.

18. The compound of claim 17, wherein $R^1$ is H, or a pharmaceutically acceptable salt thereof.

19. The compound of claim 16, wherein $R^1$ is H, $CH_2OH$, $CH_2F$, $CHF_2$, $CH=CH_2$, $C\equiv CH$, CN, $CH_2CH=CH_2$, $N_3$, $CH_3$, or $CH_2CH_3$, $R^2$ is OH or O-benzyl, $R^3$ is F or $N_3$, or a combination thereof, or a pharmaceutically acceptable salt thereof.

20. The compound of claim 16, wherein $R^5$ is $NH_2$ and $R^4$ is =O, or a pharmaceutically acceptable salt thereof.

21. The compound of claim 16, wherein $R^4$ is H or =O; and $R^5$ is selected from the group consisting of H, $NH_2$, NHMe, NHcPr, OH, OMe, Cl, Br, I, SMe, F, $N_3$, CN, $CF_3$, and $SO_2Me$, or a pharmaceutically acceptable salt thereof.

22. The compound of claim 21, wherein $R^4$ is =O, $R^5$ is H or $NH_2$, or a combination thereof, or a pharmaceutically acceptable salt thereof.

23. The compound of claim 16, wherein $R^6$ is H, benzyl, or

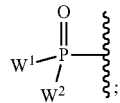

wherein $W^2$ is OH and $W^1$ is a group of the Formula Ia:

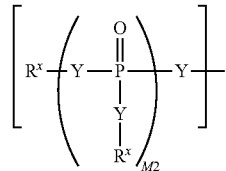

Formula Ia wherein:
Y is O;
M2 is 2; and
each $R^x$ is H,
or a pharmaceutically acceptable salt thereof.

24. The compound of claim 23, wherein $R^6$ is H, or a pharmaceutically acceptable salt thereof.

25. The compound of claim 16, wherein $R^1$ is H, $R^2$ is OH and $R^3$ is F, or a pharmaceutically acceptable salt thereof.

* * * * *